(12) United States Patent
Turunen et al.

(10) Patent No.: US 10,988,763 B2
(45) Date of Patent: Apr. 27, 2021

(54) SINGLE-STRANDED RNA-EDITING OLIGONUCLEOTIDES

(71) Applicant: ProQR Therapeutics II B.V., Leiden (NL)

(72) Inventors: Janne Juha Turunen, Leiden (NL); Petra Geziena De Bruijn, Leiden (NL); Bart Klein, Leiden (NL); Roxana Simona Redis, Leiden (NL); Lenka Van Sint Fiet, Leiden (NL)

(73) Assignee: PROQR THERAPEUTICS II B.V., Leiden (NL)

( * ) Notice: Subject to any disclaimer, the term of this patent is extended or adjusted under 35 U.S.C. 154(b) by 0 days.

(21) Appl. No.: 16/309,954

(22) PCT Filed: Jun. 22, 2017

(86) PCT No.: PCT/EP2017/065467
§ 371 (c)(1),
(2) Date: Dec. 14, 2018

(87) PCT Pub. No.: WO2017/220751
PCT Pub. Date: Dec. 28, 2017

(65) Prior Publication Data
US 2019/0330622 A1    Oct. 31, 2019

(30) Foreign Application Priority Data

Jun. 22, 2016 (GB) .................................. 1610923
Aug. 30, 2016 (GB) .................................. 1614669
Feb. 21, 2017 (GB) .................................. 1702755
Apr. 20, 2017 (GB) .................................. 1706292

(51) Int. Cl.
*C12N 15/11* (2006.01)
*C12N 15/10* (2006.01)
*A61K 31/7125* (2006.01)

(52) U.S. Cl.
CPC ........ *C12N 15/111* (2013.01); *A61K 31/7125* (2013.01); *C12N 15/102* (2013.01); *C12N 2310/11* (2013.01); *C12N 2310/321* (2013.01); *C12N 2310/3521* (2013.01); *C12N 2310/3527* (2013.01); *C12N 2320/30* (2013.01)

(58) Field of Classification Search
None
See application file for complete search history.

(56) References Cited

U.S. PATENT DOCUMENTS

| 10,676,737 B2 | 6/2020 | Klein et al. |
| 2019/0218552 A1 | 7/2019 | Turunen et al. |
| 2019/0352641 A1 | 11/2019 | Aalto et al. |
| 2020/0199586 A1 | 6/2020 | Klein et al. |

FOREIGN PATENT DOCUMENTS

WO    WO-2016/097212 A1    6/2016

OTHER PUBLICATIONS

International Search Report for PCT/EP2017/065467, dated Sep. 15, 2017 (5 pages).
Lamond et al. (1993) "Antisense oligonucleotides made of 2'-O-alkylRNA: their properties and applications in RNA biochemistry," FEBS Letters, 325(1, 2): 123-127.
Lancaster et al. (2014) "Organogenesis in a Dish: Modeling Development and Disease Using Organoid Technologies," Science, 345(6194): 1247125.
Montiel-Gonzalez et al. (2013) "Correction of Mutations Within the Cystic Fibrosis Transmembrane Conductance Regulator by Site-Directed RNA Editing," PNAS, 110(45): 18285-18290.
Sala et al. (2009) "Tissue-Engineered Small Intestine and Stomach Form from Autologous Tissue in a Preclinical Large Animal Model," J Surg Res.; 156(2): 205-12.
Sato et al. (2011) "Long-term Expansion of Epithelial Organoids From Human Colon, Adenoma, Adenocarcinoma, and Barrett's Epithelium," Gastroenterology, 141(5): 1762-72.
Schneider et al. (2014) "Optimal GuideRNAs for Re-directing Deaminase Activity of hADAR1 and hADAR2 in *Trans*," Nucleic Acids Res., 42(10):e87.
Schneider et al. (2014) "Supporting Information: Optimal GuideRNAs for Re-directing Deaminase Activity of hADAR1 and hADAR2 in Trans," URL: http://nar.oxfordjournals.org/content/suppl/2014/04/05/gku272.DC1/nar-03496-met-g-2013-File007.pdf (15 pages).
Stafforst et al. (2012) "An RNA-deaminase Conjugate Selectively Repairs Point Mutations," Angewandte Chemie Int. Ed., 51(44): 11166-11169.
Stafforst et al. (2012) "Supporting Information: An RNA-deaminase Conjugate Selectively Repairs Point Mutations," URL: https://onlinelibrary.wiley.com/action/downloadSupplement?doi=10.1002%2Fanie.201206489&file=anie_201206489_sm_miscellaneous_information.pdf (23 pages).
Stefl et al. (2006) "Structure and Specific RNA Binding of ADAR2 Double-Stranded RNA Binding Motifs," Structure 14(2): 345-355.

(Continued)

*Primary Examiner* — Sean McGarry
(74) *Attorney, Agent, or Firm* — Goodwin Procter LLP

(57) ABSTRACT

The invention relates to antisense oligonucleotides that are capable of bringing about specific editing of a target nucleotide (adenosine) in a target RNA in a eukaryotic cell, wherein said oligonucleotide does not, in itself, form an intramolecular hairpin or stem-loop structure, and wherein said oligonucleotide comprises a cytidine (a non-complementary nucleotide) or a uridine in position opposite to the target adenosine to be edited in the target RNA region.

20 Claims, 14 Drawing Sheets

Specification includes a Sequence Listing.

(56) References Cited

OTHER PUBLICATIONS

Tian et al. (2011) "A Structural Determinant Required for RNA Editing," Nucleic Acids Res. 39(13): 5669-5681.
Vogel et al. (2014) "Improving Site-Directed RNA Editing in Vitro and in Cell Culture by Chemical Modification of the GuideRNA," Angewandte Chemie Int. Ed., 53:6267-6271.
Woolf et al. (1995) "Toward the Therapeutic Editing of Mutated RNA Sequences," PNAS, 92: 8298-8302.
Written Opinion for PCT/EP2017/065467, dated Sep. 15, 2017 (5 pages).

Fig. 1

A: AON ADAR56

3'-UGACCUUUUGAUGGACAAGGUAC̲CGGUUGUGAACAGUGAUGAAAG-5'
5'-CUACUGGAAAACUACCUGUUCCAUAGCCAACACUUGUCACUACUUUCUCUUAUGGUGUUCAAUGCUUU-3'

B: AON ADAR57

3'-UGACCUUUUGU̲UGGACAAGGUAC̲CGGUUGUGAAGAGUGAUGAAAG-5'
5'-CUACUGGAAAACUACCUGUUCCAUAGCCAACACUUGUCACUACUUUCUCUUAUGGUGUUCAAUGCUUU-3'

C: AON ADAR58

3'-UGACCUUAAC̲AUGGACAAGGUAC̲CGGUUGUGAACAGC̲UC̲UGAAAG-5'
5'-CUACUGGAAAACUACCUGUUCCAUAGCCAACACUUGUCACUACUUUCUCUUAUGGUGUUCAAUGCUUU-3'

D: AON ADAR59

3'-GAUGGACAAGGUAC̲CGGUUGUGAAGAGUC̲AUGAAAGAGAAUAGAAGAAGUUAC-5'
5'-CUACUGGAAAACUACCUGUUCCAUAGCCAACACUUGUCACUACUUUCUCUUAUGGUGUUCAAUGCUUU-3'

Fig. 5
A
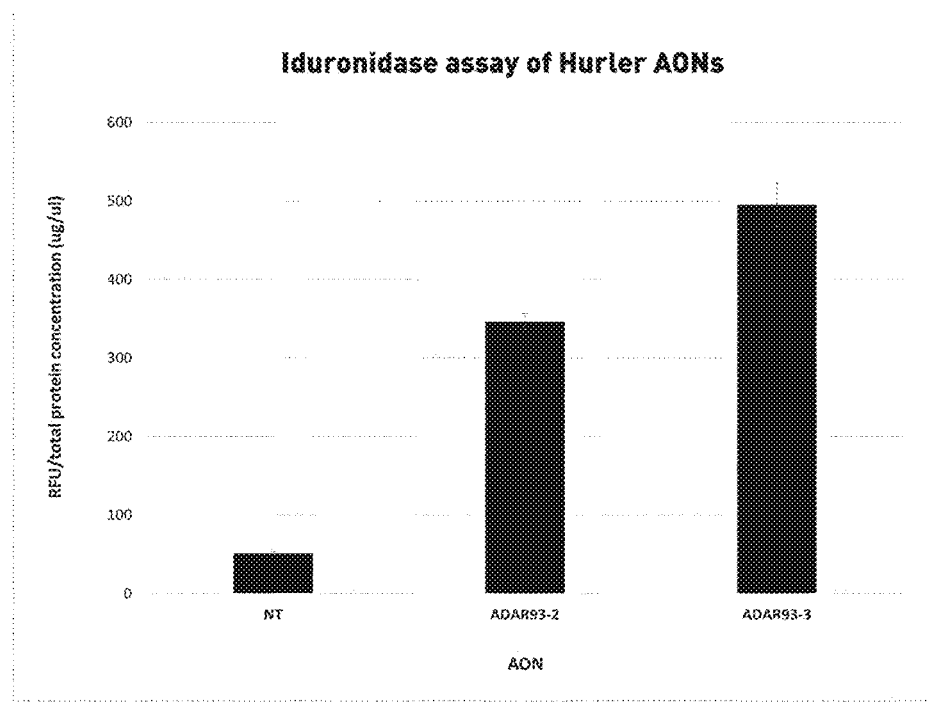
B
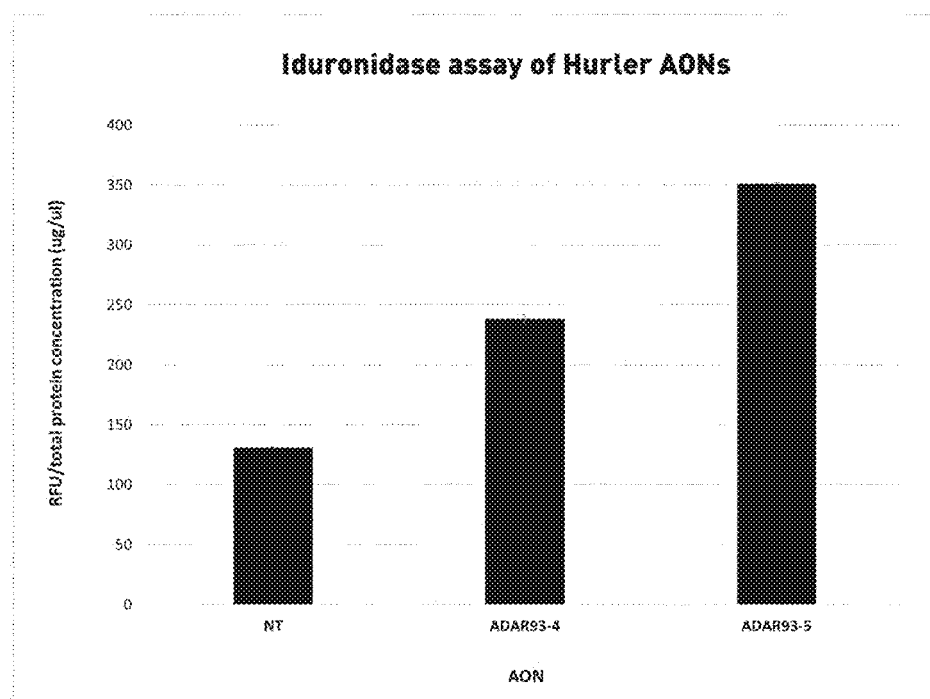

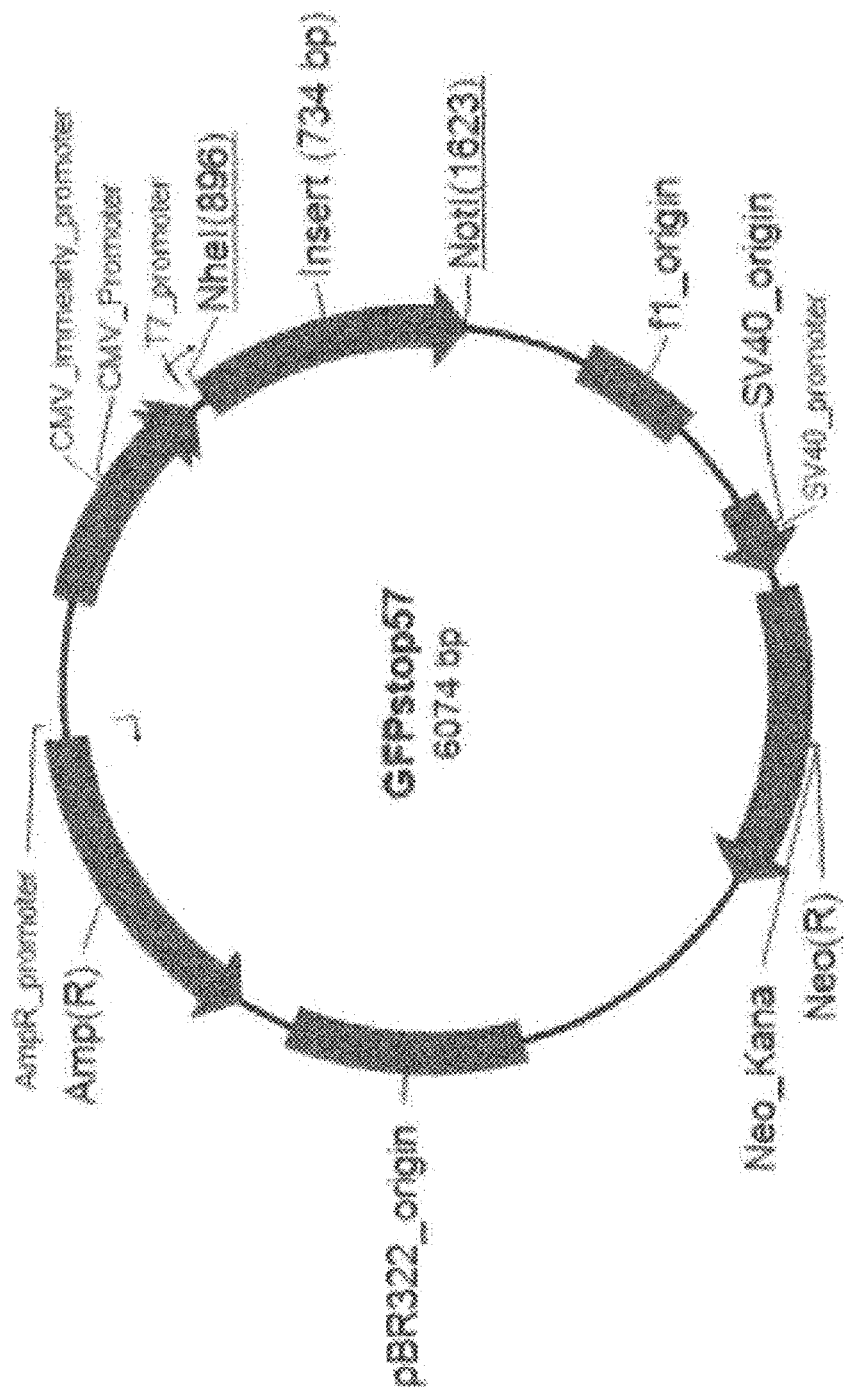

5'...AAGAUCUCUUUUGCCAAGAAGUAGCGCCUUUCCCUAUGGAGUACCCCAGUCCCUUCCCCCCUUGGCUCAGUCCCUGAAGGUAAGUCCCCUUAG
     K  I  S  F  A  K  K  *  R  L  S  L  W  S  T  P  V  P  S  P  P  P  L  A  Q  S  L  K  V  S  P  P  *

↓ RNA editing

5'...AAGAUCUCUUUUGCCAAGAAGUGGCGCCUUUCCCUAUGGAGUACCCCAGUCCCUUCCCCCCUUGGCUCAGUCCCUGAAGGUAAGUCCCCUUAG
     K  I  S  F  A  K  K  W  R  L  S  L  W  S  T  P  V  P  S  P  P  P  L  A  Q  S  L  K  V  S  P  P  *

B

5'...AAGAUCUCUUUUGCCAAGAAGUAGCGCCUUUCCU---AUGGAGUACCCCAGUCCCUUCCCCCCUUGGCUCAGUCCCUGAAGGUAAGUCCCCUUAG

3'-AGGAAACGGUUCUUCACCGUGGAAAGGAGGGUAC-GGAUG-5'    (ADAR87-1; SEQ ID NO:18)

3'-AGGAAACGGUUCUUCACCGUGGAAAGGGA---UACCUCAUGGAGUCAG-5'    (ADAR89-1; SEQ ID NO:19)

3'-AGGAAACGGUUCUUCACCGUGGAAAGGA---UACCUCAUGGAGUCAG-5'    (ADAR89-2; SEQ ID NO:32)

3'-AGGAAACGGUUCUUCACCGUGGAAAGAGA---UUCCUCAUGGAGUCAG-5'    (ADAR94-1; SEQ ID NO:33)

SEQUENCE LISTING

```
<160> NUMBER OF SEQ ID NOS: 38

<210> SEQ ID NO 1
<211> LENGTH: 45
<212> TYPE: RNA
<213> ORGANISM: Artificial Sequence
<220> FEATURE:
<223> OTHER INFORMATION: Antisense oligonucleotide

<400> SEQUENCE: 1
ugaccuuuug auggacaagg uaccgguugu gaacagugau gaaag            45

<210> SEQ ID NO 2
<211> LENGTH: 45
<212> TYPE: RNA
<213> ORGANISM: Artificial Sequence
<220> FEATURE:
<223> OTHER INFORMATION: Antisense oligonucleotide

<400> SEQUENCE: 2
ugaccuuuug uuggacaagg uaccgguugu gaagagugau gaaag            45

<210> SEQ ID NO 3
<211> LENGTH: 45
<212> TYPE: RNA
<213> ORGANISM: Artificial Sequence
<220> FEATURE:
<223> OTHER INFORMATION: Antisense oligonucleotide

<400> SEQUENCE: 3
ugaccuuaac auggacaagg uaccgguugu gaacagcucu gaaag            45

<210> SEQ ID NO 4
<211> LENGTH: 53
<212> TYPE: RNA
<213> ORGANISM: Artificial Sequence
<220> FEATURE:
<223> OTHER INFORMATION: Antisense oligonucleotide

<400> SEQUENCE: 4
gauggacaag guaccgguug ugaagaguca ugaaagagaa uagaagaagu uac   53

<210> SEQ ID NO 5
<211> LENGTH: 68
<212> TYPE: RNA
<213> ORGANISM: Artificial Sequence
<220> FEATURE:
<223> OTHER INFORMATION: Antisense oligonucleotide

<400> SEQUENCE: 5
cuacuggaaa acuaccuguu ccauagccaa cacugucac uacuuucucu uaugguguuc   60
aaugcuuu                                                          68
```

<210> SEQ ID NO 6
<211> LENGTH: 17
<212> TYPE: RNA
<213> ORGANISM: Unknown
<220> FEATURE:
<223> OTHER INFORMATION: boxB RNA hairpin sequence

<400> SEQUENCE: 6
ggcccugaaa aagggcc                                                  17

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
agagggtgaa ggtgatgcaa                                               20

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
gggcatggca ctcttgaaaa                                               20

<210> SEQ ID NO 9
<211> LENGTH: 734
<212> TYPE: DNA
<213> ORGANISM: Unknown
<220> FEATURE:
<223> OTHER INFORMATION: GFPstop57

<400> SEQUENCE: 9
gctagcatgg ccagcaaagg agaagaactt ttcactggag ttgtcccaat tcttgttgaa      60
ttagatggtg atgttaatgg gcacaaattt tctgtcagtg gagagggtga aggtgatgct     120
acatacggaa agcttaccct taaatttatt tgcactactg gaaaactacc tgttccatag     180
ccaacacttg tcactacttt ctcttatggt gttcaatgct tttcccgtta ccgatcat       240 atgaaacggc atgactttt caagagtgcc atgcccgaag ttatgtaca ggaacgcact       300 atatctttca aagatgacgg gaactacaag acgcgtgctg aagtcaagtt tgaaggtgat     360
acccttgtta tcgtatcga gttaaaaggt attgatttta agaagatgg aaacattctc      420 ggacacaaac tcgagtacaa ctataactca cacaatgtat acatcacggc agacaaacaa     480
aagaatggaa tcaaagctaa cttcaaaatt cgccacaaca ttgaagatgg atccgttcaa     540
ctagcagacc attatcaaca aaatactcca attggcgatg gccctgtcct tttaccagac     600
aaccattacc tgtcgacaca atctgccctt tcgaaagatc ccaacgaaaa gcgtgaccac     660
atggtccttc ttgagtttgt aactgctgct gggattacac atggcatgga tgagctctac     720
aaataagcgg ccgc                                                      734

<210> SEQ ID NO 10
<211> LENGTH: 238
<212> TYPE: PRT
<213> ORGANISM: Unknown
<220> FEATURE:

<223> OTHER INFORMATION: GFPstop57

<400> SEQUENCE: 10

```
Met Ala Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 11
<211> LENGTH: 68
<212> TYPE: DNA
<213> ORGANISM: Artificial Sequence
<220> FEATURE:
<223> OTHER INFORMATION: exon 9 of the Idua gene

<400> SEQUENCE: 11
atggagaaca actctaggca gaggtctcaa aggctggggc tgtgttggac agcaatcata    60
cagtgggt                                                            68

<210> SEQ ID NO 12
<211> LENGTH: 68
<212> TYPE: RNA
<213> ORGANISM: Artificial Sequence
<220> FEATURE:
<223> OTHER INFORMATION: Antisense oligonucleotide

<400> SEQUENCE: 12
auggagaaca acucuaggca gaggucucaa aggcuggggc uguguuggac agcaaucaua    60
cagugggu                                                            68

<210> SEQ ID NO 13

```
<211> LENGTH: 50
<212> TYPE: RNA
<213> ORGANISM: Artificial Sequence
<220> FEATURE:
<223> OTHER INFORMATION: Antisense oligonucleotide

<400> SEQUENCE: 13
ccucuuguug agacccgucu ccagaguuuc gaccccgac acaaccuguc        50

<210> SEQ ID NO 14
<211> LENGTH: 46
<212> TYPE: RNA
<213> ORGANISM: Artificial Sequence
<220> FEATURE:
<223> OTHER INFORMATION: Antisense oligonucleotide

<400> SEQUENCE: 14
uuguugagac ccgucuccag aguuccgac cccgacacaa ccuguc           46

<210> SEQ ID NO 15
<211> LENGTH: 50
<212> TYPE: RNA
<213> ORGANISM: Artificial Sequence
<220> FEATURE:
<223> OTHER INFORMATION: Antisense oligonucleotide

<400> SEQUENCE: 15
ccucuuguug agacccgucu ccagagauuc agaccccgac aaccccguc       50

<210> SEQ ID NO 16
<211> LENGTH: 99
<212> TYPE: RNA
<213> ORGANISM: Unknown
<220> FEATURE:
<223> OTHER INFORMATION: Small Nuclear Ribonucleoprotein Polypeptide A

<400> SEQUENCE: 16
aagaucucuu uugccaagaa guagcgccuu ucccuaugga guaccccagu cccuucccc    60 ccucccuugg cucagucccu gaagguaagu ccccuuag                           99

<210> SEQ ID NO 17
<211> LENGTH: 99
<212> TYPE: RNA
<213> ORGANISM: Artificial Sequence
<220> FEATURE:
<223> OTHER INFORMATION: Edited Small Nuclear Ribonucleoprotein
      Polypeptide A

<400> SEQUENCE: 17
aagaucucuu uugccaagaa guggcgccuu ucccuaugga guaccccagu cccuucccc    60 ccucccuugg cucagucccu gaagguaagu ccccuuag                           99

<210> SEQ ID NO 18
<211> LENGTH: 40
<212> TYPE: RNA
<213> ORGANISM: Artificial Sequence
<220> FEATURE:
<223> OTHER INFORMATION: Antisense oligonucleotide

<400> SEQUENCE: 18
guaggcaugg gaggaaaagg ugccacuucu uggcaaagga             40

<210> SEQ ID NO 19
<211> LENGTH: 45
<212> TYPE: RNA
```

```
<213> ORGANISM: Artificial Sequence
<220> FEATURE:
<223> OTHER INFORMATION: Antisense oligonucleotide

<400> SEQUENCE: 19
gacugaggua cuccauaggg aaaggugcca cuucuuggca aagga          45

<210> SEQ ID NO 20
<211> LENGTH: 47
<212> TYPE: RNA
<213> ORGANISM: Artificial Sequence
<220> FEATURE:
<223> OTHER INFORMATION: Antisense oligonucleotide

<400> SEQUENCE: 20
uccuuugcca agaaguggca ccuuuuccuc ccaugccuac uccuucc        47

<210> SEQ ID NO 21
<211> LENGTH: 19
<212> TYPE: DNA
<213> ORGANISM: Artificial Sequence
<220> FEATURE:
<223> OTHER INFORMATION: PCR primer

<400> SEQUENCE: 21
gccttcgtgg agtttgaca                                       19

<210> SEQ ID NO 22
<211> LENGTH: 20
<212> TYPE: DNA
<213> ORGANISM: Artificial Sequence
<220> FEATURE:
<223> OTHER INFORMATION: PCR primer

<400> SEQUENCE: 22
acacacggct ctgagaaggt                                      20

<210> SEQ ID NO 23
<211> LENGTH: 21
<212> TYPE: DNA
<213> ORGANISM: Artificial Sequence
<220> FEATURE:
<223> OTHER INFORMATION: PCR primer

<400> SEQUENCE: 23
cgtggagttt gacaatgaag t                                    21

<210> SEQ ID NO 24
<211> LENGTH: 50
<212> TYPE: RNA
<213> ORGANISM: Artificial Sequence
<220> FEATURE:
<223> OTHER INFORMATION: Antisense oligonucleotide

<400> SEQUENCE: 24
ccucuuguug agacccgucu ccagaguuuc gaccccgac acaaccuguc      50

<210> SEQ ID NO 25
<211> LENGTH: 50
<212> TYPE: RNA
<213> ORGANISM: Artificial Sequence
<220> FEATURE:
<223> OTHER INFORMATION: Antisense oligonucleotide

<400> SEQUENCE: 25
ccucuuguug agaccugucu ccagaguuuc gaccccgac acaaccuguc      50
```

<210> SEQ ID NO 26
<211> LENGTH: 54
<212> TYPE: RNA
<213> ORGANISM: Artificial Sequence
<220> FEATURE:
<223> OTHER INFORMATION: Antisense oligonucleotide

<400> SEQUENCE: 26
ccucuuguug agacccgucu ccagagauuc agaccucgac aacuccuguc guua         54

<210> SEQ ID NO 27
<211> LENGTH: 43
<212> TYPE: RNA
<213> ORGANISM: Artificial Sequence
<220> FEATURE:
<223> OTHER INFORMATION: Antisense oligonucleotide

<400> SEQUENCE: 27
ccucuuguug agacccgucu ccagaguuuc cgaccucgac aca                     43

<210> SEQ ID NO 28
<211> LENGTH: 43
<212> TYPE: RNA
<213> ORGANISM: Artificial Sequence
<220> FEATURE:
<223> OTHER INFORMATION: Antisense oligonucleotide

<400> SEQUENCE: 28
acacagcucc agccuuugag accucugccc agaguuguuc ucc                     43

<210> SEQ ID NO 29
<211> LENGTH: 43
<212> TYPE: RNA
<213> ORGANISM: Artificial Sequence
<220> FEATURE:
<223> OTHER INFORMATION: Antisense oligonucleotide

<400> SEQUENCE: 29
acacagcucc agccuuugag accucugccc agaauuguuc ucc                     43

<210> SEQ ID NO 30
<211> LENGTH: 43
<212> TYPE: RNA
<213> ORGANISM: Artificial Sequence
<220> FEATURE:
<223> OTHER INFORMATION: Antisense oligonucleotide

<400> SEQUENCE: 30
acacaucucc agccuaugac accucugccc agaguuguuc ucc                     43

<210> SEQ ID NO 31
<211> LENGTH: 43
<212> TYPE: RNA
<213> ORGANISM: Artificial Sequence
<220> FEATURE:
<223> OTHER INFORMATION: Antisense oligonucleotide

<400> SEQUENCE: 31
acacaucucc agccuaugac accucugccc agaauuguuc ucc                     43

<210> SEQ ID NO 32
<211> LENGTH: 45
<212> TYPE: RNA
<213> ORGANISM: Artificial Sequence
<220> FEATURE:

```
<223> OTHER INFORMATION: Antisense oligonucleotide

<400> SEQUENCE: 32
gacugaggua cuccauaggg aaaggugcca cuucuuggca aagga                45

<210> SEQ ID NO 33
<211> LENGTH: 45
<212> TYPE: RNA
<213> ORGANISM: Artificial Sequence
<220> FEATURE:
<223> OTHER INFORMATION: Antisense oligonucleotide

<400> SEQUENCE: 33
gacugaggua cuccuuagag aaaggugcca cuucuuggca aagga                45

<210> SEQ ID NO 34
<211> LENGTH: 53
<212> TYPE: RNA
<213> ORGANISM: Artificial Sequence
<220> FEATURE:
<223> OTHER INFORMATION: Antisense oligonucleotide

<400> SEQUENCE: 34
cauugaggaa gguaagagaa agugcugaga gguguuggcc auggagcagg uag        53

<210> SEQ ID NO 35
<211> LENGTH: 71
<212> TYPE: RNA
<213> ORGANISM: Artificial Sequence
<220> FEATURE:
<223> OTHER INFORMATION: Antisense oligonucleotide

<400> SEQUENCE: 35
aucauuggcu gacacuuucg aacacaugau agaagagcug uuggaugagg accagaaagu  60
ucggcccaau g                                                     71

<210> SEQ ID NO 36
<211> LENGTH: 52
<212> TYPE: RNA
<213> ORGANISM: Artificial Sequence
<220> FEATURE:
<223> OTHER INFORMATION: Antisense oligonucleotide

<400> SEQUENCE: 36
cugugaaagc uugugcauua ucuucucgac aaccacucc uggucuuuca ag          52

<210> SEQ ID NO 37
<211> LENGTH: 52
<212> TYPE: RNA
<213> ORGANISM: Artificial Sequence
<220> FEATURE:
<223> OTHER INFORMATION: Antisense oligonucleotide
<220> FEATURE:
<221> NAME/KEY: N
<222> LOCATION: 15
<223> OTHER INFORMATION: N is inosine

<400> SEQUENCE: 37
cugugaaagc uuguncauua ucuucucgac aaccacucc uggucuuuca ag          52

<210> SEQ ID NO 38
<211> LENGTH: 52
<212> TYPE: RNA
<213> ORGANISM: Artificial Sequence
<220> FEATURE:
<223> OTHER INFORMATION: Antisense oligonucleotide
```

```
<400> SEQUENCE: 38
cugugaaagc uugugcauua ucuucucguc aaacuacucc uguaauuuca ag          52
```

SINGLE-STRANDED RNA-EDITING OLIGONUCLEOTIDES

RELATED APPLICATIONS

This application is a §371 National Stage Application of PCT/EP2017/065467, filed Jun. 22, 2017, which claims priority to and the benefit of United Kingdom patent application No. 1610923.3, filed Jun. 22, 2016, United Kingdom patent application No. 1614669.8, filed Aug. 30, 2016, United Kingdom patent application No. 1702755.8, filed Feb. 21, 2017, and United Kingdom patent application No. 1706292.8, filed Apr. 20, 2017, the entire disclosures of each of which are incorporated herein by reference for all purposes.

FIELD OF THE INVENTION

The invention relates to the field of medicine. More in particular, it relates to the field of RNA editing, whereby an RNA sequence is targeted by a single-stranded antisense oligonucleotide to specifically correct a mutation in the RNA sequence.

BACKGROUND OF THE INVENTION

RNA editing is a natural process through which eukaryotic cells alter the sequence of their RNA molecules, often in a site-specific and precise way, thereby increasing the repertoire of genome encoded RNAs by several orders of magnitude. RNA editing enzymes have been described for eukaryotic species throughout the animal and plant kingdoms, and these processes play an important role in managing cellular homeostasis in metazoans from the simplest life forms (such as *Caenorhabditis elegans*) to humans. Examples of RNA editing are adenosine (A) to inosine (I) conversions and cytidine (C) to uridine (U) conversions, which occur through enzymes called adenosine deaminase and cytidine deaminase, respectively. The most extensively studied RNA editing system is the adenosine deaminase enzyme.

Adenosine deaminase is a multi-domain protein, comprising—depending on the enzyme in question—2 to 3 double-stranded RNA recognition domains and a catalytic domain. The recognition domain recognizes a specific double stranded RNA (dsRNA) sequence and/or conformation, whereas the catalytic domain converts an adenosine (A) into inosine (I) in a nearby, more or less predefined, position in the target RNA, by deamination of the nucleobase. Inosine is read as guanine by the translational machinery of the cell, meaning that, if an edited adenosine is in a coding region of an mRNA or pre-mRNA, it can recode the protein sequence.

A to I conversions may also occur in 5' non-coding sequences of a target mRNA, creating new translational start sites upstream of the original start site, which gives rise to N-terminally extended proteins, or in the 3' UTR or other non-coding parts of the transcript, which may affect the processing and/or stability of the RNA. In addition, A to I conversions may take place in splice elements in introns or exons in pre-mRNAs, thereby altering the pattern of splicing. As a consequence thereof, exons may be included or skipped. The adenosine deaminases are part of a family of enzymes referred to as Adenosine Deaminases acting on RNA (ADAR), including human deaminases hADAR1, hADAR2 and hADAR3.

The use of oligonucleotides to edit a target RNA applying adenosine deaminase has been described (e.g. Montiel-Gonzalez et al. PNAS 2013, 110(45):18285-18290; Vogel et al. 2014. Angewandte Chemie Int Ed 53:267-271; Woolf et al. 1995. PNAS 92:8298-8302). Montiel-Gonzalez et al. (2013) described the editing of a target RNA using a genetically engineered fusion protein, comprising an adenosine deaminase domain of the hADAR2 protein, fused to a bacteriophage lambda N protein, which recognises the boxB RNA hairpin sequence. The natural dsRNA binding domains of hADAR2 had been removed to eliminate the substrate recognition properties of the natural ADAR and replace it by the boxB recognition domain of lambda N-protein. The authors created an antisense oligonucleotide comprising a 'guide RNA' part that is complementary to the target sequence for editing, fused to a boxB portion for sequence specific recognition by the N-domain-deaminase fusion protein. By doing so, it was elegantly shown that the guide RNA oligonucleotide faithfully directed the adenosine deaminase fusion protein to the target site, resulting in guide RNA-directed site-specific A to I editing of the target RNA. These guide RNAs, disclosed in Montiel-Gonzalez et al. (2013), are longer than 50 nucleotides, which is generally too long for therapeutic applications (difficulties in manufacturing and cell entry). A disadvantage of this method in a therapeutic setting is also the need for a fusion protein consisting of the boxB recognition domain of bacteriophage lambda N-protein, genetically fused to the adenosine deaminase domain of a truncated natural ADAR protein. It requires target cells to be either transduced with the fusion protein, which is a major hurdle, or that target cells are transfected with a nucleic acid construct encoding the engineered adenosine deaminase fusion protein for expression. The latter requirement constitutes no minor obstacle when editing is to be achieved in a multicellular organism, such as in therapy against human disease to correct a genetic disorder.

Vogel et al. (2014) disclosed editing of RNA coding for eCFP and Factor V Leiden, using a benzylguanine substituted guide RNA and a genetically engineered fusion protein, comprising the adenosine deaminase domains of ADAR1 or 2 (lacking the dsRNA binding domains) genetically fused to a SNAP-tag domain (an engineered O6-alkylguanine-DNA-alkyl transferase). Although the genetically engineered artificial deaminase fusion protein could be targeted to a desired editing site in the target RNAs in HeLa cells in culture, through its SNAP-tag domain which is covalently linked to a guide RNA through a 5'-terminal O6-benzylguanine modification, this system suffers from similar drawbacks as the genetically engineered ADARs described by Montiel-Gonzalez et al. (2013), in that it is not clear how to apply the system without having to genetically modify the ADAR first and subsequently transfect or transduct the cells harboring the target RNA, to provide the cells with this genetically engineered protein. Clearly, this system is not readily adaptable for use in humans, e.g. in a therapeutic setting.

Woolf et al. (1995) disclosed a simpler approach, using relatively long single stranded antisense RNA oligonucleotides (25-52 nucleotides in length) wherein the longer oligonucleotides (34-mer and 52-mer) could promote editing of the target RNA by endogenous ADAR because of the double stranded nature of the target RNA and the oligonucleotide hybridizing thereto. The oligonucleotides of Woolf et al. (1995) that were 100% complementary to the target RNA sequences only appeared to function in cell extracts or in amphibian (*Xenopus*) oocytes by microinjection, and suffered from severe lack of specificity: nearly all adenosines in the target RNA strand that was complementary to the antisense oligonucleotide were edited. An oligonucleotide, 34 nucleotides in length, wherein each nucleotide comprised a 2'O-methyl modification, was tested and shown to be inactive in Woolf et al. (1995). In order to provide stability against nucleases, a 34-mer RNA, modified with 2'O-methyl-modified phosphorothioate nucleotides at the 5'- and 3'-terminal 5 nucleotides, was also tested. It was shown that the central unmodified region of this oligonucleotide could promote editing of the target RNA by endogenous ADAR, with the terminal modifications providing protection against exonuclease degradation. Woolf et al. (1995) does not achieve deamination of a specific target adenosine in the target RNA sequence. As mentioned, nearly all adenosines opposite an unmodified nucleotide in the antisense oligonucleotide were edited (therefore nearly all adenosines opposite nucleotides in the central unmodified region, if the 5'- and 3'-terminal 5 nucleotides of the antisense oligonucleotide were modified, or nearly all adenosines in the target RNA strand if no nucleotides were modified). It is known that ADAR may act on any dsRNA. Through a process sometimes referred to as 'promiscuous editing', the enzyme will edit multiple A's in the dsRNA. Hence, there is a need for methods and means that circumvent such promiscuous editing and that only target specified adenosines in a target RNA sequence for therapeutic applicability. Vogel et al. (2014) showed that such off-target editing can be suppressed by using 2'-O-methyl-modified nucleotides in the oligonucleotide at positions opposite to the adenosines that should not be edited, and use a non-modified nucleotide directly opposite to the specifically targeted adenosine on the target RNA. However, the specific editing effect at the target nucleotide has not been shown to take place in that article without the use of recombinant ADAR enzymes that have covalent bonds with the antisense oligonucleotide.

It is noted that yet another editing technique exists which uses oligonucleotides, known as the CRISPR/Cas9 system. However, this editing complex acts on DNA. It also suffers from the same drawback as the engineered ADAR systems described above, because it requires co-delivery to the target cell of the CRISPR/Cas9 enzyme, or an expression construct encoding the same, together with the guide oligonucleotide.

In view of the above, there remains a need for new techniques and compounds that can utilise endogenous cellular pathways and naturally available ADAR enzymes to specifically edit endogenous nucleic acids in mammalian cells, even in whole organisms, without the problems associated with the methods of the prior art.

SUMMARY OF THE INVENTION

The present invention does away with the drawbacks of the methods according to the prior art by providing a targeted approach to RNA editing using, in one embodiment, an antisense oligonucleotide (AON) capable of forming a double stranded complex with a target RNA in a cell, for the deamination of a specific target adenosine in said target RNA by a mammalian ADAR enzyme present in said cell; wherein said AON is complementary to a target RNA comprising the target adenosine, said AON optionally comprising one or more mismatches, wobbles and/or bulges with said target RNA; wherein the AON comprises one or more nucleotides with a sugar modification, provided that the nucleotide opposite the target adenosine comprises a ribose with a 2'-OH group or a deoxyribose with a 2'-H group; wherein the AON does not comprise a (non-complementary) portion (non-complementary to the target and non-complementary in respect of itself) that is capable of forming an intramolecular stem-loop structure that is capable of binding a mammalian ADAR enzyme; wherein the AON does not include a 5'-terminal O6-benzylguanine or a 5'-terminal amino modification; and wherein the AON is not covalently linked to a SNAP-tag domain. The AON of the present invention is preferably in its basic structure a single-stranded RNA-editing oligonucleotide. In a preferred embodiment, the nucleotide opposite the target adenosine is a cytidine or a uridine, more preferably a cytidine. In yet another preferred aspect, the nucleotide directly 5' and/or 3' from the nucleotide opposite the target adenosine comprise a ribose with a 2'-OH group, or a deoxyribose with a 2'-H group. To prevent degradation by endonucleases as much as possible, preferably all other nucleotides in said AON besides the nucleotide that is opposite the target adenosine and one or both of the nucleotides directly adjacent to the opposing nucleotide comprise a 2'-O-alkyl group, preferably a 2'-O-methyl group. In another preferred aspect, each nucleotide that is opposite an adenosine in the target RNA sequence comprises a 2'-O-alkyl group, preferably a 2'-O-methyl group, except for the nucleotide opposite the target adenosine, which comprises a ribose with a 2'-OH group. In yet also a preferred embodiment, the AON comprises, besides the cytidine opposite the target adenosine (which may be the single mismatch) at least one additional mismatch or wobble base pair with the target sequence. The presence of the at least one additional mismatch and/or wobble base pair may add to the RNA editing efficiency possibly because it adds to the altered on/off rate of the AON with its target molecule and/or to the binding and/or recognition of the ADAR molecule to the dsRNA, also depending on the target sequence. As outlined herein, one particular preferred position for an additional mismatch and/or wobble base pair between AON and target sequence (besides the preferred C-A of the target position) is the position at four nucleotides upstream (towards 5') of the target adenosine in the target sequence. It is also disclosed herein that, depending on the target sequence, additional mismatches and/or wobble base pairs, as well as additional bulges (non-pairing and small out-looping stretches of nucleotides) may add to the RNA editing efficiency. It is therefore a preferred aspect of the present invention to have additional bulges, mismatches and/or wobbles between the AON and the target sequence, besides the difference between the cytidine opposite the target adenosine (or besides the uridine opposite the target adenosine, which is then not a mismatch but which may be preferred for certain target sequences). In a preferred aspect the cell in which the AON is introduced is a human cell. In yet another preferred aspect the AON of the present invention comprises at least one phosphorothioate linkage, preferably wherein the 2, 3, 4, 5, or 6 terminal nucleotides of the 5' and 3' terminus of the AON are linked with phosphorothioate linkages, even more preferably wherein the terminal five nucleotides at the 5' and 3' terminus are linked with (in that case four) phosphorothioate linkages. In one embodiment the AON of the present invention does not have a 5' cap. In another embodiment of the invention, the AON is not a 17-mer or a 20-mer. In another embodiment of the invention the portion of the AON that is complementary to the target RNA sequence is longer than 17 nucleotides, or shorter than 14 nucleotides. The present invention also relates to a pharmaceutical composition comprising the AON according to the invention, and a pharmaceutically acceptable carrier.

The present invention also relates to the AON according to the invention for use in the treatment or prevention of a genetic disorder, preferably selected from the group consisting of: Cystic fibrosis, Hurler Syndrome, alpha-1-antitrypsin (A1AT) deficiency, Parkinson's disease, Alzheimer's disease, albinism, Amyotrophic lateral sclerosis, Asthma, ß-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermylosis bullosa, Fabry disease, Factor V Leiden associated disorders, Familial Adenomatous, Polyposis, Galactosemia, Gaucher's Disease, Glucose-6-phosphate dehydrogenase, Haemophilia, Hereditary Hematochromatosis, Hunter Syndrome, Huntington's disease, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-eso1 related cancer, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, and cancer.

The invention also relates to a method for the deamination of a specific target adenosine present in a target RNA sequence in a cell, said method comprising the steps of: providing said cell with an AON according to the invention; allowing uptake by the cell of said AON; allowing annealing of said AON to the target RNA sequence; allowing a mammalian ADAR enzyme comprising a natural dsRNA binding domain as found in the wild type enzyme to deaminate said target adenosine in said target RNA sequence to an inosine; and identifying the presence of said inosine in the RNA sequence.

In preferred embodiments of the present invention the target RNA sequence encodes CFTR (e.g. to edit a 1784G>A mutation), CEP290 (e.g. to edit a c.2991+1655A>G mutation), alpha1-antitrypsin (A1AT; e.g. to edit a 9989G>A mutation; or a 1096G>A mutation), LRRK2 (e.g. to edit a G6055 mutation), BDNF (e.g. to repair the Val66Met mutation on the RNA level), or wherein the target RNA is encoded by the IDUA gene (e.g. to edit a c.1205G>A (W402X) mutation).

BRIEF DESCRIPTION OF THE DRAWINGS

FIG. 1 shows the complementarity of antisense oligonucleotides (upper strands) to the GFPstop target sequence (lower strands). In panels A to D, a portion of the sequence of the target RNA is shown 5' to 3' (lower strand in each panel), with the target adenosine (A) in bold. The sequence of the oligonucleotides in the upper strand is shown from 3' to 5', with the mismatches, wobbles, and 'bulges' underlined. Chemical modifications are not shown. The lower strand in all panels is the same (SEQ ID NO:5) and reflects only a portion of the GFP target sequence. The UAG in the target sequence is a stop codon (from 5' to 3'), which is, when the A is edited to an I (read as a G), converted to UGG representing a Trp codon allowing the GFP protein to be completely translated into a functional protein. A. upper strand AON ADAR56 (SEQ ID NO:1); B. upper strand AON ADAR57 (SEQ ID NO:2); C. upper strand AON ADAR58 (SEQ ID NO:3); D. upper strand AON ADAR59 (SEQ ID NO:4).

FIG. 5 shows the same enzymatic assay as in FIG. 4 after using two pairs of antisense oligonucleotides that only differ with each other in the mismatch with the target sequence at position 4, upstream of the targeting sequence, indicating the positive effect of this specific additional bulge between oligonucleotide and target sequence.

FIG. 10(A) shows the map of the expression plasmid carrying the GFPstop57 insert. The nucleic acid sequence and the resulting amino acid sequence of the GFP is provided in (B) and shows that the constructs encodes a protein of 57 amino acids, because of the TAG stop at triplet 58. The adenosine in this TAG is edited to an inosine (read as a guanosine), resulting in a TGG codon, as disclosed herein.

FIG. 11(A) shows the 5' terminal part of the RNA sequence of the Small Nuclear Ribonucleoprotein Polypeptide A (SNRPA) gene (SEQ ID NO:16). In the upper strand the coding sequence is underlined up to the UAG stop codon (bold). RNA editing of the A within the stop codon to an I (read as a G) results in UGG coding for tryptophan (W); the edited sequence is also provided (SEQ ID NO:17). This read-through then in theory results in a protein that is 25 amino acids longer when translated up to the subsequent stop codon (also in bold). (B) shows the same 5' terminal part of the SNRPA as given in (A). Below the coding sequence the AON sequences of ADAR87-1, ADAR89-1, ADAR89-2 and ADAR94-1 are given. Bulges, wobbles and mismatches are underlined. The cytidine opposite the to-be-targeted adenosine is given in a larger font. The three nucleosides in the Central Triplet 5'-CCA-3' in ADAR89-2 and ADAR94-1 are DNA, whereas all other nucleosides in these oligonucleotides are RNA.

DETAILED DESCRIPTION OF THE INVENTION

Figure 2:
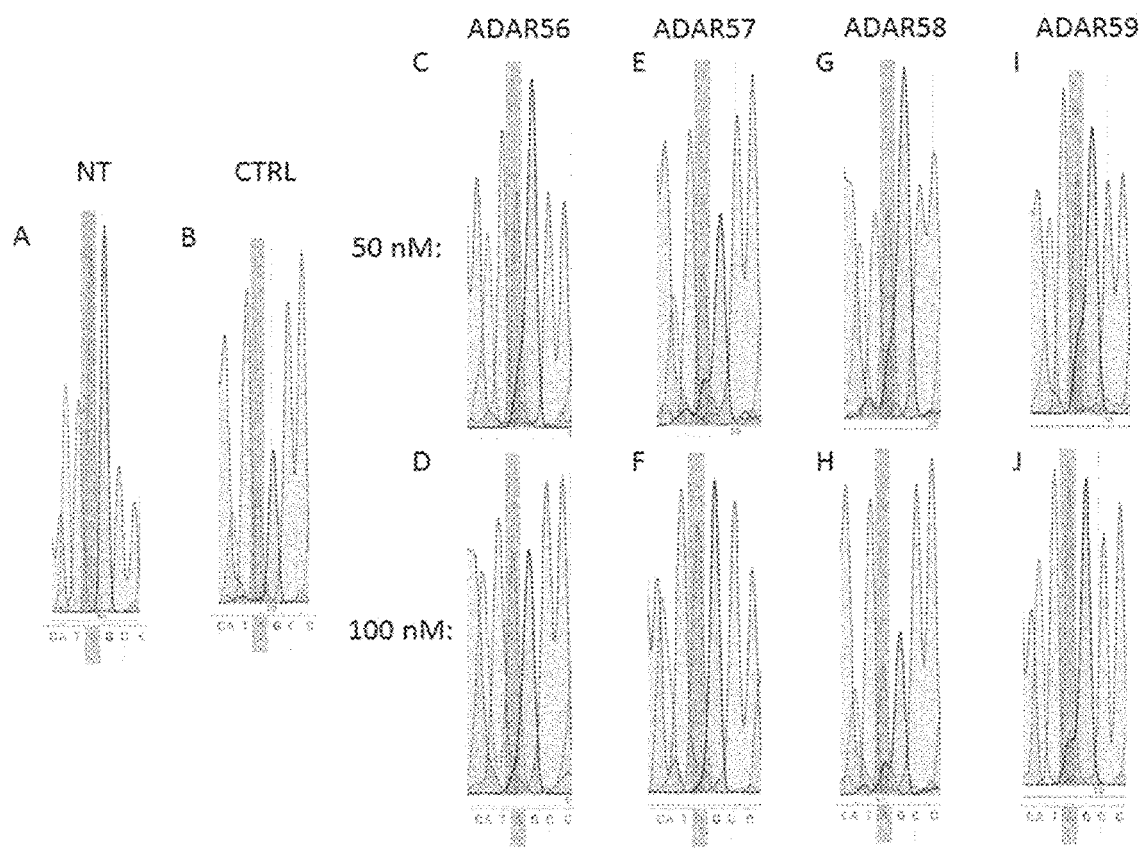
FIG. 2 shows the efficiency of editing, assayed by sequence analysis. The chromatograms (A to J) show the nucleotide frequency at the target site (highlighted above the center A) and neighboring nucleotides. The nucleotide identity of the peaks is indicated by the same color as in the sequence below the chromatograms, wherein G's are represented in black. In panel (A) results from non-treated cells (NT) are shown, and in panel (B) only transfection reagent was used (CTRL). AONs ADAR56 through ADAR59 were used at 50 nM or 100 nM concentrations, as indicated panels (C) to (J). There is a clear increase in G signal above the central A (shown as a 'shoulder' in the neighboring G signal, whereas no shoulder is observed in the controls), which shows that in all four cases, using any of the four AONs, RNA editing has taken place at that position.

WO 2016/097212 discloses antisense oligonucleotides (AONs) for the targeted editing of RNA, wherein the AONs are characterized by a sequence that is complementary to a target RNA sequence (therein referred to as the 'targeting portion') and by the presence of a stem-loop structure (therein referred to as the 'recruitment portion'), which is preferably non-complementary to the target RNA. Such oligonucleotides are referred to as 'self-looping AONs'. The recruitment portion acts in recruiting a natural ADAR enzyme present in the cell to the dsRNA formed by hybridization of the target sequence with the targeting portion. Due to the recruitment portion there is no need for conjugated entities or presence of modified recombinant ADAR enzymes. WO 2016/097212 describes the recruitment portion as being a stem-loop structure mimicking either a natural substrate (e.g. the GluB receptor) or a Z-DNA structure known to be recognized by the dsRNA binding regions of ADAR enzymes. A stem-loop structure can be an intermolecular stem-loop structure, formed by two separate nucleic acid strands, or an intramolecular stem loop structure, formed within a single nucleic acid strand. The stem-loop structure of the recruitment portion as described in WO 2016/097212 is an intramolecular stem-loop structure, formed within the AON itself, and able to attract ADAR.

The AONs of the present invention do not comprise a recruitment portion as described in WO 2016/097212. The AONs of the present invention do not comprise a portion that is capable of forming an intramolecular stem-loop structure. The AONs of the present invention are shorter, which makes them cheaper to produce, easier to use and easier to manufacture. Furthermore, they do not have the disadvantage of potentially sequestering ADAR enzymes from their normal function in the cell. Unexpectedly, the inventors of the present invention found that AONs that are complementary to a target RNA for deaminating a target adenosine present in a target RNA sequence to which the AON is complementary, but—importantly—lack a recruitment portion as described above, appeared still capable of harnessing ADAR enzymes present in the cell to edit the target adenosine. In a preferred aspect the AON of the present invention comprises a mismatch at the position of the target adenosine, wherein the opposite nucleotide in the AON is a cytidine. Also when a uridine is opposite the target adenosine (which would in fact not be a mismatch), the AON is capable of bringing about deamination of the target adenosine. It was found by the inventors of the present invention that additional mismatches, wobbles and/or out-looping bulges (caused by nucleotides in the antisense oligonucleotide that do not form perfect base pairs with the target RNA according to the Watson-Crick base pairing rules) are tolerable, in some cases preferable, but in increasing numbers not always essential for specific targeted editing of the target RNA sequence. The number of mismatches, wobbles or bulges in the AON of the present invention (when it hybridises to its RNA target sequence) may be zero (when the nucleoside opposite the target adenosine is a uridine and the rest of the AON is also 100% complementary to the target sequence), may be one (which may be the one mismatch formed at the target adenosine position, when a cytosine is the opposite nucleoside, or some other position in the AON) or more (either including or not including the (mis)match at the target adenosine), depending on the length of the AON. Additional mismatches, wobbles or bulges may be upstream as well as downstream of the target adenosine. In a particular preferred embodiment, a mismatch or wobble is present at the position four nucleotides upstream (towards the 5' end) from the targeted adenosine, which may then also be the only mismatch or wobble, when a uridine pairs with the target adenosine, or which may then be an additional mismatch or wobble when the nucleoside opposite the target adenosine is a cytidine. The bulges or mismatches may be at a single position (caused by one mismatching, wobble or bulge base pair) or a series of nucleotides that are not fully complementary (caused by more than one consecutive mismatching or wobble base pair or bulge, preferably two or three consecutive mismatching and/or wobble base pairs and/or bulges).

In any case, the AONs according to the present invention have certain advantages over the oligonucleotides described in WO 2016/097212, in that there is no need for hairpin or stem-loop structures, which allow the AONs of the present invention to be (considerably) shorter. Moreover, the oligonucleotides described in WO 2016/097212 bear the potential risk of sequestering ADAR enzyme present in the cell. By sequestering in this context is meant that a natural ADAR protein may bind to the oligonucleotides described in WO 2016/097212 even in the absence of the formation of a dsRNA complex between the targeting portion of the oligonucleotide and the target RNA. This direct binding of ADAR to the oligonucleotides described in WO 2016/097212 (due to the presence of an intramolecular stem-loop structure), in the absence of target RNA sequences does not take place when using the AONs of the present invention, which do not comprise a portion that is capable of forming an intramolecular stem-loop structure. Although the oligonucleotides described in WO 2016/097212 may have certain applications, there are many instances where the presence of the hairpin and/or (stem-) loop structures is preferably avoided.

The present invention hence relates to an antisense oligonucleotide (AON) capable of forming a double stranded complex with a target RNA in a cell, for the deamination of a target adenosine present in the target RNA by an ADAR enzyme present in the cell, wherein the AON is complementary to a target RNA region comprising the target adenosine, and the AON optionally comprises one or more mismatches, wobbles and/or bulges with the complementary target RNA region; the AON comprises one or more nucleotides with one or more sugar modifications, provided that the nucleotide opposite the target adenosine comprises a ribose with a 2'-OH group, or a deoxyribose with a 2'-H group; the AON does not comprise a portion that is capable of forming an intramolecular stem-loop structure that is capable of binding an ADAR enzyme; the AON does not include a 5'-terminal O6-benzylguanine modification; the AON does not include a 5'-terminal amino modification; and the AON is not covalently linked to a SNAP-tag domain.

In a preferred aspect the nucleotide in the AON opposite the target adenosine is not RNA but DNA, and in an even more preferred aspect, the nucleotide opposite the target adenosine as well as the nucleotide 5' and/or 3' of the nucleotide opposite the target adenosine are DNA nucleotides, while the remainder (not DNA) of the nucleotides in the AON are preferably 2'-O-alkyl modified ribonucleotides. When two nucleotides are DNA all others may be RNA and may be 2'-O methyl modified, whereas in particular aspects the third nucleotide in the triplet opposite the target adenosine may be RNA and non-modified, as long as the nucleotide opposite the target adenosine is not 2'-O methyl modified. In one particular aspect the invention relates to an AON capable of forming a double stranded complex with a target RNA in a cell, for the deamination of a target adenosine present in the target RNA by an enzyme present in the cell (likely an ADAR enzyme), wherein the AON is (partly) complementary to a target RNA region comprising the target adenosine, wherein the nucleotide opposite the target adenosine comprises a deoxyribose with a 2'-H group, wherein the nucleotide 5' and/or 3' of the nucleotide opposite the target adenosine also comprises a deoxyribose with a 2'-H group, and the remainder of the AON comprises ribonucleosides, preferably all with 2'-O methyl modifications.

In another aspect, the invention relates to an AON capable of forming a double stranded complex with a target RNA in a cell, for the deamination of a target adenosine present in the target RNA by an ADAR enzyme present in the cell, wherein the AON is complementary to a target RNA region comprising the target adenosine, and the AON optionally comprises one or more mismatches, wobbles and/or bulges with the complementary target RNA region; the AON comprises one or more nucleotides with one or more sugar modifications, provided that the nucleotide opposite the target adenosine comprises a ribose with a 2'-OH group or a deoxyribose with a 2'-H group; the AON does not comprise a portion that is capable of forming an intramolecular stem-loop structure that is capable of binding an ADAR enzyme; and the AON is not a 17-mer or a 20-mer.

In another aspect the invention relates to an AON capable of forming a double stranded complex with a target RNA in a cell, for the deamination of a target adenosine present in the target RNA by an ADAR enzyme present in the cell, wherein the AON is complementary to a target RNA region comprising the target adenosine, and the AON optionally comprises one or more mismatches, wobbles and/or bulges with the complementary target RNA region; the AON comprises one or more nucleotides with one or more sugar modifications, provided that the nucleotide opposite the target adenosine comprises a ribose with a 2'-OH group, or a deoxyribose with a 2'-H group; the AON does not comprise a portion that is capable of forming an intramolecular stem-loop structure that is capable of binding an ADAR enzyme; and the AON is longer than 17 nucleotides, or shorter than 14 nucleotides.

In yet another aspect the invention relates to an AON capable of forming a double stranded complex with a target RNA in a cell, for the deamination of a target adenosine present in the target RNA by an ADAR enzyme present in the cell, wherein the AON is complementary to a target RNA region comprising the target adenosine; the AON comprises one or more nucleotides with one or more sugar modifications, provided that the nucleotide opposite the target adenosine comprises a ribose with a 2'-OH group, or a deoxyribose with a 2'-H group; the AON does not comprise a portion that is capable of forming an intramolecular stem-loop structure that is capable of binding an ADAR enzyme; the AON optionally comprises 1, 2, 3, 4, 5, 6, 7, 8, 9 or 10 mismatches, wobbles and/or bulges with the complementary target RNA region. Preferably, the nucleotide opposite the target adenosine is a cytidine, a deoxycytidine, a uridine, or a deoxyuridine. When the nucleotide opposite the target adenosine is a cytidine or a deoxycytidine, the AON comprises at least one mismatch with the target RNA. When the nucleotide opposite the target adenosine is a uridine or a deoxyuridine, the AON may be 100% complementary and not have any mismatches, wobbles or bulges in relation to the target RNA. However, in a preferred aspect one or more additional mismatches, wobbles and/or bulges are present between AON and target RNA whether the nucleotide opposite the target adenosine is a cytidine, a deoxycytidine, a uridine, or a deoxyuridine. In another preferred embodiment, the nucleotide directly 5' and/or 3' from the nucleotide opposite the target adenosine comprises a ribose with a 2'-OH group, or a deoxyribose with a 2'-H group, or a mixture of these two (triplet consists then of DNA-DNA-DNA; DNA-DNA-RNA; RNA-DNA-DNA; RNA-DNA-RNA; or RNA-RNA-RNA; preferably wherein the middle nucleoside does not have a 2'-O methyl modification (when RNA) and either or both surrounding nucleosides also do not have a 2'-O methyl modification). It is then preferred that all other nucleotides in the AON then do have a 2'-O-alkyl group, preferably a 2'-O-methyl group, or a 2'-O-methoxyethyl (2'-MOE) group, or any modification as disclosed herein. The AONs of the present invention preferably comprise at least one phosphorothioate linkage. In a further preferred aspect, the 2, 3, 4, 5, or 6 terminal nucleotides of the 5' and 3' terminus of the AON are linked with phosphorothioate linkages. More preferably, the terminal 5 nucleotides at the 5' and 3' terminus are linked with phosphorothioate linkages. In one particular embodiment of the present invention, the AON is longer than 10, 11, 12, 13, 14, 15, 16 or 17 nucleotides. Preferably, the AON is shorter than 100 nucleotides, more preferably shorter than 60 nucleotides, and even more preferably, the AON comprises 18 to 70 nucleotides, 18 to 60 nucleotides, or 18 to 50 nucleotides. The invention also relates to a pharmaceutical composition comprising the AON according to the invention, and a pharmaceutically acceptable carrier. The invention also relates to an AON according to the invention for use in the treatment or prevention of a genetic disorder, preferably selected from the group consisting of: Cystic fibrosis, Hurler Syndrome, alpha-1-antitrypsin (A1AT) deficiency, Parkinson's disease, Alzheimer's disease, albinism, Amyotrophic lateral sclerosis, Asthma, ß-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermylosis bullosa, Fabry disease, Factor V Leiden associated disorders, Familial Adenomatous, Polyposis, Galactosemia, Gaucher's Disease, Glucose-6-phosphate dehydrogenase, Haemophilia, Hereditary Hematochromatosis, Hunter Syndrome, Huntington's disease, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-esol related cancer, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, and cancer. In another aspect the invention relates to a use of an AON according to the invention in the manufacture of a medicament for the treatment or prevention of a genetic disorder, preferably selected from the group consisting of: Cystic fibrosis, Hurler Syndrome, alpha-1-antitrypsin (A1AT) deficiency, Parkinson's disease, Alzheimer's disease, albinism, Amyotrophic lateral sclerosis, Asthma, ß-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermylosis bullosa, Fabry disease, Factor V Leiden associated disorders, Familial Adenomatous, Polyposis, Galactosemia, Gaucher's Disease, Glucose-6-phosphate dehydrogenase, Haemophilia, Hereditary Hematochromatosis, Hunter Syndrome, Huntington's disease, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-esol related cancer, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, and cancer. In yet another embodiment of the invention, it relates to a method for the deamination of at least one target adenosine present in a target RNA in a cell, the method comprising the steps of providing the cell with an AON according to the invention; allowing uptake by the cell of the AON; allowing annealing of the AON to the target RNA; allowing an ADAR enzyme comprising a natural dsRNA binding domain as found in the wild type enzyme to deaminate the target adenosine in the target RNA to an inosine; and optionally identifying the presence of the inosine in the targeted RNA, preferably wherein the last step comprises sequencing the targeted RNA sequence; assessing the presence of a functional, elongated, full length and/or wild type protein when the target adenosine is located in a UGA or UAG stop codon, which is edited to a UGG codon through the deamination; assessing the presence of a functional, elongated, full length and/or wild type protein when two target adenosines are located in a UAA stop codon, which is edited to a UGG codon through the deamination of both target adenosines; assessing whether splicing of the pre-mRNA was altered by the deamination; or using a functional read-out, wherein the target RNA after the deamination encodes a functional, full length, elongated and/or wild type protein. In another embodiment, the invention relates to an AON or a method according to the invention, wherein the target RNA sequence encodes CFTR (e.g. to edit a 1784G>A mutation), CEP290 (e.g. to edit a c.2991+1655A>G mutation), alpha1-antitrypsin (A1AT; e.g. to edit a 9989G>A mutation; or a 1096G>A mutation), LRRK2 (e.g. to edit a G6055 mutation), BDNF (e.g. to repair the Val66Met mutation on the RNA level), or wherein the target RNA is encoded by the IDUA gene (e.g. to edit a c.1205G>A (W402X) mutation).

It is an important aspect of the invention that the AON comprises one or more nucleotides with one or more sugar modifications. Thereby, a single nucleotide of the AON can have one, or more than one sugar modification. Within the AON, one or more nucleotide(s) can have such sugar modification(s).

It is also an important aspect of the invention that the nucleotide within the AON of the present invention that is opposite to the nucleotide that needs to be edited does not contain a 2'-O-methyl modification (herein often referred to as a 2'-OMe group, or as 2'-O-methylation) and preferably comprises a 2'-OH group, or is a deoxyribose with a 2'-H group. It is preferred that the nucleotides that are directly 3' and/or 5' of this nucleotide (the 'neighbouring nucleotides') also lack such a chemical modification, although it is believed that it is tolerated that one of these neighbouring nucleotides may contain a 2'-O-alkyl group (such as a 2'-O-methyl group), but preferably not both. Either one, or both neighbouring nucleotides may be 2'-OH or a compatible substitution (as defined herein).

Another important aspect of the AON of the present invention is that it does not have a portion that is complementary to the target RNA or the RNA region that comprises the target adenosine that allows the AON in itself to fold into an intramolecular hairpin or other type of (stem-) loop structure (herein also referred to as "auto-looping" or "self-looping"), and which may potentially act as a structure that sequesters ADAR. In one aspect, the single stranded AON of the present invention is fully complementary with the target RNA, although it preferably does not perfectly pair on at least one position, which is at the position of the target adenosine, where the opposite nucleoside is then preferably a cytidine. The single-stranded RNA editing oligonucleotides of the present invention may also have one or more mismatches, wobbles or bulges (no opposite nucleoside) with the target sequence, at other positions than at the target adenosine position. These wobbles, mismatches and/or bulges of the AON of the present invention with the target sequence do not prevent hybridization of the oligonucleotide to the target RNA sequence, but add to the RNA editing efficiency by the ADAR present in the cell, at the target adenosine position. The person skilled in the art is able to determine whether hybridization under physiological conditions still does take place. Preferred single-stranded RNA editing oligonucleotides of the present invention do not include a 5'-terminal O6-benzylguanine or a 5'-terminal amino modification, and are not covalently linked to a SNAP-tag domain (an engineered O6-alkylguanine-DNA-alkyl transferase), in contrast to Vogel et al. (2014). The SNAP-tag domain is derived from the human DNA repair protein O6-alkylguanine-DNA-alkyl transferase (AGT) and can be covalently labelled in living cells using O6-benzylguanine derivatives. Vogel et al. (2014) discloses guide RNAs with a total length of either 20 or 17 nucleotides, wherein the first three nucleotides at the 5' end do not bind to the target RNA sequence, but link the guide RNA to the SNAP-tag domain. The portion of the guide RNA which binds to the target RNA sequence is therefore either 14 or 17 nucleotides in length. Guide RNAs, of the same lengths, with a 5'-terminal amino modification in place of the 5'-terminal O6-benzylguanine modification are also disclosed in Vogel et al. (2014), however only very little, or no deamination or the target RNA sequence was detected. In one embodiment, the AON of the present invention comprises fewer than four mismatches and/or wobbles with the target RNA sequence. Similarly, a preferred AON of the present invention does not include a boxB RNA hairpin sequence, in contrast to Montiel-Gonzalez et al (2013). The boxB RNA hairpin sequence used in Montiel-Gonzalez et al. (2013) is a short stretch of RNA of 17 nucleotides (with the sequence GGCCCUGAAAAAGGGCC, SEQ ID NO:6) that is recognized by the bacteriophage lambda N-protein. Transcription of downstream genes in the early operons of bacteriophage requires a promoter-proximal element known as nut. This site acts in cis in the form of RNA to assemble a transcription anti-termination complex which is composed of a bacteriophage lambda N protein and host factors. The nut-site RNA contains a small stem-loop structure called boxB. The boxB RNA hairpin sequence is known in the art as an interrupted palindrome with the potential to form a hairpin (stem-loop) structure. Its sequence varies among relatives of bacteriophage lambda which encode distinct genome-specific N homologues. Neither Vogel et al. (2014), nor Montiel-Gonzalez et al (2013) use a mammalian ADAR enzyme present in the cell, wherein the ADAR enzyme comprises its natural dsRNA binding domain as found in the wild type enzyme. Vogel et al. (2014) uses a genetically engineered fusion protein comprising the adenosine deaminase domain of ADAR1 or 2 fused to a SNAP-tag domain and Montiel-Gonzalez et al uses a genetically engineered fusion protein comprising the adenosine deaminase domain of the hADAR2 protein, fused to the boxB recognition domain of bacteriophage lambda N protein. In contrast to the prior art, the AON of the present invention uses a mammalian ADAR enzyme present in the cell, wherein the ADAR enzyme comprises its natural dsRNA binding domain as found in the wild type enzyme. There is therefore no need to incorporate a boxB RNA hairpin sequence, a 5'-terminal O6-benzylguanine, a 5'-terminal amino modification, or a SNAP-tag domain into the AON of the present invention, to allow recruitment of ADAR. The AONs according to the present invention therefore have certain advantages over the oligonucleotides described in Vogel et al. (2014) and Montiel-Gonzalez et al (2013). The AONs according to the present invention can utilise endogenous cellular pathways and naturally available ADAR enzymes to specifically edit a target adenosine in a target RNA sequence. In one embodiment, an AON of the invention is not covalently linked to a human O6-alkylguanine-DNA-alkyl transferase. Preferably, an AON of the invention is not covalently linked to a polypeptide. In another aspect of the AON of the present invention, the AON does not have a 5' cap. In eukaryotes, the 5' cap consists of a guanine nucleotide connected to the RNA via a 5' to 5' triphosphate linkage. This guanosine is methylated on the 7 position and is referred to as a 7-methylguanosine. As disclosed herein, the single-stranded RNA editing-inducing oligonucleotides of the invention are capable of deamination of a specific target adenosine nucleotide in a target RNA sequence. Ideally, only one adenosine is deaminated. Alternatively 1, 2, or 3 adenosine nucleotides are deaminated, but preferably only one. Taking the features of the AONs of the present invention together, there is no need for modified recombinant ADAR expression, there is no need for conjugated entities attached to the AON, or the presence of long recruitment portions that are not complementary to the target RNA sequence. Besides that, the AON of the present invention does allow for the specific deamination of a target adenosine present in the target RNA sequence to an inosine by a natural ADAR enzyme comprising a natural dsRNA binding domain as found in the wild type enzyme, without the risk of promiscuous editing elsewhere in the RNA/AON complex.

The recruitment of cytidine deaminase to a target site works in the same way as for the adenosine deaminases hADAR1 and hADAR2. However, cytidine deaminases have different binding requirements and recognize different structures in their target RNA sequences that determine editing of the cytidine. One particularly well studied cytidine deaminase is human Apobec1. The general principle of RNA editing using an oligonucleotide construct to target an editing site and to recruit a resident, naturally present, editing entity remains the same for cytidine deaminases, and is part of the invention disclosed and claimed herein.

Analysis of natural targets of ADAR enzymes indicated that these generally include mismatches between the two strands that form the RNA helix edited by ADAR1 or ADAR2. It has been suggested that these mismatches enhance the specificity of the editing reaction (Stefl et al. 2006. Structure 14(2):345-355; Tian et al. 2011. Nucleic Acids Res 39(13):5669-5681). Characterization of optimal patterns of paired/mismatched nucleotides between the AONs and the target RNA also appears crucial for development of efficient ADAR-based AON therapy. An improved feature of the AONs of the present invention is the use of specific nucleotide modifications at predefined spots to ensure stability as well as proper ADAR binding and activity. These changes may vary and may include modifications in the backbone of the AON, in the sugar moiety of the nucleotides as well as in the nucleobases. They may also be variably distributed throughout the sequence of the AON, depending on the target and on secondary structures. Specific chemical modifications may be needed to support interactions of different amino acid residues within the RNA-binding domains of ADAR enzymes, as well as those in the deaminase domain. For example, phosphorothioate linkages between nucleotides, and/or 2'-O-methyl modifications may be tolerated in some parts of the AON, while in other parts they should be avoided so as not to disrupt crucial interactions of the enzyme with the phosphate and/or 2'-OH groups. Part of these design rules are guided by the published structures of ADAR2, while others have to be defined empirically. Different preferences may exist for ADAR1 and ADAR2. The modifications should also be selected such that they prevent degradation of the AONs. Specific nucleotide modifications may also be necessary to enhance the editing activity on substrate RNAs where the target sequence is not optimal for ADAR editing. Previous work has established that certain sequence contexts are more amenable to editing. For example, the target sequence 5'-UAG-3' (with the target A in the middle) contains the most preferred nearest-neighbor nucleotides for ADAR2, whereas a 5'-CAA-3' target sequence is disfavored (Schneider et al. 2014. Nucleic Acids Res 42(10):e87). The recent structural analysis of ADAR2 deaminase domain hints at the possibility of enhancing editing by careful selection of the nucleotides that are opposite to the target trinucleotide. For example, the 5'-CAA-3' target sequence, paired to a 3'-GCU-5' sequence on the opposing strand (with the A-C mismatch formed in the middle), is disfavored because the guanosine base sterically clashes with an amino acid side chain of ADAR2. However, here it is postulated that a smaller nucleobase, such as inosine, could potentially fit better into this position without causing steric clashes, while still retaining the base-pairing potential to the opposing cytidine. Modifications that could enhance activity of suboptimal sequences include the use of backbone modifications that increase the flexibility of the AON or, conversely, force it into a conformation that favors editing.

Definitions of Terms as Used Herein

The terms 'adenine', 'guanine', 'cytosine', 'thymine', 'uracil' and 'hypoxanthine' (the nucleobase in inosine) as used herein refer to the nucleobases as such.

The terms 'adenosine', 'guanosine', 'cytidine', 'thymidine', 'uridine' and 'inosine', refer to the nucleobases linked to the (deoxy)ribosyl sugar.

The term 'nucleoside' refers to the nucleobase linked to the (deoxy)ribosyl sugar.

The term 'nucleotide' refers to the respective nucleobase-(deoxy)ribosyl-pholinker, as well as any chemical modifications of the ribose moiety or the phospho group. Thus the term would include a nucleotide including a locked ribosyl moiety (comprising a 2'-4' bridge, comprising a methylene group or any other group, well known in the art), a nucleotide including a linker comprising a phosphodiester, phosphotriester, phosphoro(di)thioate, methylphosphonates, phosphoramidate linkers, and the like.

Sometimes the terms adenosine and adenine, guanosine and guanine, cytosine and cytidine, uracil and uridine, thymine and thymidine, inosine and hypo-xanthine, are used interchangeably to refer to the corresponding nucleobase, nucleoside or nucleotide.

Sometimes the terms nucleobase, nucleoside and nucleotide are used interchangeably, unless the context clearly requires differently. The terms 'ribonucleoside' and 'deoxyribonucleoside', or 'ribose' and 'deoxyribose' are as used in the art.

Whenever reference is made to an 'oligonucleotide', both oligoribonucleotides and deoxyoligoribonucleotides are meant unless the context dictates otherwise. Whenever reference is made to an 'oligoribonucleotide' it may comprise the bases A, G, C, U or I. Whenever reference is made to a 'deoxyoligoribonucleotide' it may comprise the bases A, G, C, T or I. In a preferred aspect, the AON of the present invention is an oligoribonucleotide that may comprise chemical modifications.

Whenever reference is made to nucleotides in the oligonucleotide construct, such as cytosine, 5-methylcytosine, 5-hydroxymethylcytosine and β-D-Glucosyl-5-hydroxymethylcytosine are included; when reference is made to adenine, N6-Methyladenine and 7-methyladenine are included; when reference is made to uracil, dihydrouracil, 4-thiouracil and 5-hydroxymethyluracil are included; when reference is made to guanine, 1-methylguanine is included.

Whenever reference is made to nucleosides or nucleotides, ribofuranose derivatives, such as 2'-desoxy, 2'-hydroxy, and 2'-O-substituted variants, such as 2'-O-methyl, are included, as well as other modifications, including 2'-4' bridged variants.

Whenever reference is made to oligonucleotides, linkages between two mono-nucleotides may be phosphodiester linkages as well as modifications thereof, including, phosphodiester, phosphotriester, phosphoro(di)thioate, methylphosphonate, phosphor-amidate linkers, and the like.

The term 'comprising' encompasses 'including' as well as 'consisting', e.g. a composition 'comprising X' may consist exclusively of X or may include something additional, e.g. X+Y.

The term 'about' in relation to a numerical value x is optional and means, e.g. x±10%.

The word 'substantially' does not exclude 'completely', e.g. a composition which is 'substantially free from Y' may be completely free from Y. Where relevant, the word 'substantially' may be omitted from the definition of the invention.

The term "complementary" as used herein refers to the fact that the AON hybridizes under physiological conditions to the target sequence. The term does not mean that each and every nucleotide in the AON has a perfect pairing with its opposite nucleotide in the target sequence. In other words, while an AON may be complementary to a target sequence, there may be mismatches, wobbles and/or bulges between AON and the target sequence, while under physiological conditions that AON still hybridizes to the target sequence such that the cellular RNA editing enzymes can edit the target adenosine. The term "substantially complementary" therefore also means that in spite of the presence of the mismatches, wobbles, and/or bulges, the AON has enough matching nucleotides between AON and target sequence that under physiological conditions the AON hybridizes to the target RNA. As shown herein, an AON may be complementary, but may also comprise one or more mismatches, wobbles and/or bulges with the target sequence, as long as under physiological conditions the AON is able to hybridize to its target.

The term 'downstream' in relation to a nucleic acid sequence means further along the sequence in the 3' direction; the term 'upstream' means the converse. Thus in any sequence encoding a polypeptide, the start codon is upstream of the stop codon in the sense strand, but is downstream of the stop codon in the antisense strand.

References to 'hybridisation' typically refer to specific hybridisation, and exclude non-specific hybridisation. Specific hybridisation can occur under experimental conditions chosen, using techniques well known in the art, to ensure that the majority of stable interactions between probe and target are where the probe and target have at least 70%, preferably at least 80%, more preferably at least 90% sequence identity.

The term 'mismatch' is used herein to refer to opposing nucleotides in a double stranded RNA complex which do not form perfect base pairs according to the Watson-Crick base pairing rules. Mismatched nucleotides are G-A, C-A, U-C, A-A, G-G, C-C, U-U pairs. In some embodiments AONs of the present invention comprise fewer than four mismatches, for example 0, 1 or 2 mismatches. Wobble base pairs are: G-U, I—U, I-A, and I-C base pairs.

An AON according to the present invention may be chemically modified almost in its entirety, for example by providing all nucleotides with a 2'-O-methylated sugar moiety (2'-OMe). However, the nucleotide opposite the target adenosine does not comprise the 2'-OMe modification, and in yet a further preferred aspect, at least one and in a preferred aspect both the two neighbouring nucleotides flanking each nucleotide opposing the target adenosine further do not comprise the 2'-OMe modification. Complete modification, wherein all nucleotides within the AON holds a 2'-OMe modification results in a non-functional oligonucleotide as far as RNA editing goes, presumably because it hinders the ADAR activity at the targeted position. In general, an adenosine in a target RNA can be protected from editing by providing an opposing nucleotide with a 2'-OMe group, or by providing a guanine or adenine as opposing base, as these two nucleobases are also able to reduce editing of the opposing adenosine.

Various chemistries and modification are known in the field of oligonucleotides that can be readily used in accordance with the invention. The regular internucleosidic linkages between the nucleotides may be altered by mono- or di-thioation of the phosphodiester bonds to yield phosphorothioate esters or phosphorodithioate esters, respectively. Other modifications of the internucleosidic linkages are possible, including amidation and peptide linkers. In a preferred aspect the AONs of the present invention have one, two, three, four or more phosphorothioate linkages between the most terminal nucleotides of the AON (hence, preferably at both the 5' and 3' end), which means that in the case of four phosphorothioate linkages, the ultimate five nucleotides are linked accordingly. It will be understood by the skilled person that the number of such linkages may vary on each end, depending on the target sequence, or based on other aspects, such as toxicity.

The ribose sugar may be modified by substitution of the 2'-O moiety with a lower alkyl (C1-4, such as 2'-O-Me), alkenyl (C2-4), alkynyl (C2-4), methoxyethyl (2'-MOE), or other substituent. Preferred substituents of the 2' OH group are a methyl, methoxyethyl or 3,3'-dimethylallyl group. The latter is known for its property to inhibit nuclease sensitivity due to its bulkiness, while improving efficiency of hybridization (Angus & Sproat FEBS 1993 Vol. 325, no. 1, 2, 123-7). Alternatively, locked nucleic acid sequences (LNAs), comprising a 2'-4' intramolecular bridge (usually a methylene bridge between the 2' oxygen and 4' carbon) linkage inside the ribose ring, may be applied. Purine nucleobases and/or pyrimidine nucleobases may be modified to alter their properties, for example by amination or deamination of the heterocyclic rings. The exact chemistries and formats may depend from oligonucleotide construct to oligonucleotide construct and from application to application, and may be worked out in accordance with the wishes and preferences of those of skill in the art.

The AON according to the invention should normally be longer than 10 nucleotides, preferably more than 11, 12, 13, 14, 15, 16, still more preferably more than 17 nucleotides. In one embodiment the AON according to the invention is longer than 20 nucleotides. The oligonucleotide according to the invention is preferably shorter than 100 nucleotides, still more preferably shorter than 60 nucleotides. In one embodiment the AON according to the invention is shorter than 50 nucleotides. In a preferred aspect, the oligonucleotide according to the invention comprises 18 to 70 nucleotides, more preferably comprises 18 to 60 nucleotides, and even more preferably comprises 18 to 50 nucleotides. Hence, in a most preferred aspect, the oligonucleotide of the present invention comprises 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides.

It is known in the art, that RNA editing entities (such as human ADAR enzymes) edit dsRNA structures with varying specificity, depending on a number of factors. One important factor is the degree of complementarity of the two strands making up the dsRNA sequence. Perfect complementarity of the two strands usually causes the catalytic domain of hADAR to deaminate adenosines in a non-discriminative manner, reacting more or less with any adenosine it encounters. The specificity of hADAR1 and 2 can be increased by introducing chemical modifications and/or ensuring a number of mismatches in the dsRNA, which presumably help to position the dsRNA binding domains in a way that has not been clearly defined yet. Additionally, the deamination reaction itself can be enhanced by providing an AON that comprises a mismatch opposite the adenosine to be edited. The mismatch is preferably created by providing a targeting portion having a cytidine opposite the adenosine to be edited. As an alternative, also uridines may be used opposite the adenosine, which, understandably, will not result in a 'mismatch' because U and A pair. Upon deamination of the adenosine in the target strand, the target strand will obtain an inosine which, for most biochemical processes, is "read" by the cell's biochemical machinery as a G. Hence, after A to I conversion, the mismatch has been resolved, because I is perfectly capable of base pairing with the opposite C in the targeting portion of the oligonucleotide construct according to the invention. After the mismatch has been resolved due to editing, the substrate is released and the oligonucleotide construct-editing entity complex is released from the target RNA sequence, which then becomes available for downstream biochemical processes, such as splicing and translation. Also this on/off rate is important because the targeting oligonucleotide should not be too tightly bound to the target RNA.

The desired level of specificity of editing the target RNA sequence may depend from target to target. Following the instructions in the present patent application, those of skill in the art will be capable of designing the complementary portion of the oligonucleotide according to their needs, and, with some trial and error, obtain the desired result.

The oligonucleotide of the invention will usually comprise the normal nucleotides A, G, U and C, but may also include inosine (I), for example instead of one or more G nucleotides.

To prevent undesired editing of adenosines in the target RNA sequence in the region of overlap with the oligonucleotide construct, the oligonucleotide may be chemically modified. It has been shown in the art, that 2'-O-methylation of the ribosyl-moiety of a nucleoside opposite an adenosine in the target RNA sequence dramatically reduces deamination of that adenosine by ADAR (Vogel et al. 2014). Hence, by including 2'-methoxy (2'-OMe) nucleotides in desired position of the oligonucleotide construct, the specificity of editing is dramatically improved. Other 2'-O substitutions of the ribosyl moiety, such as 2'-methoxyethyl (2'-MOE) and 2'-O-dimethylallyl groups may also reduce unwanted editing of the corresponding (opposite) adenosine in the target RNA sequence. All these modifications may be applied in the oligonucleotides of the present invention. Other chemical modifications are also readily available to the person having ordinary skill in the art of oligonucleotide synthesis and design. The synthesis of such chemically modified oligonucleotides and testing them in methods according to the invention does not pose an undue burden and other modifications are encompassed by the present invention.

RNA editing molecules present in the cell will usually be proteinaceous in nature, such as the ADAR enzymes found in metazoans, including mammals. Preferably, the cellular editing entity is an enzyme, more preferably an adenosine deaminase or a cytidine deaminase, still more preferably an adenosine deaminase. The ones of most interest are the human ADARs, hADAR1 and hADAR2, including any isoforms thereof such as hADAR1 p110 and p150. RNA editing enzymes known in the art, for which oligonucleotide constructs according to the invention may conveniently be designed, include the adenosine deaminases acting on RNA (ADARs), such as hADAR1 and hADAR2 in humans or human cells and cytidine deaminases. Human ADAR3 (hADAR3) has been described in the prior art, but reportedly has no deaminase activity. It is known that hADAR1 exists in two isoforms; a long 150 kDa interferon inducible version and a shorter, 100 kDa version, that is produced through alternative splicing from a common pre-mRNA. Consequently, the level of the 150 kDa isoform present in the cell may be influenced by interferon, particularly interferon-gamma (IFN-gamma). hADAR1 is also inducible by TNF-alpha. This provides an opportunity to develop combination therapy, whereby interferon-gamma or TNF-alpha and oligonucleotides according to the invention are administered to a patient either as a combination product, or as separate products, either simultaneously or subsequently, in any order. Certain disease conditions may already coincide with increased IFN-gamma or TNF-alpha levels in certain tissues of a patient, creating further opportunities to make editing more specific for diseased tissues.

Examples of chemical modifications in the AONs of the present invention are modifications of the sugar moiety, including by cross-linking substituents within the sugar (ribose) moiety (e.g. as in LNA or locked nucleic acids), by substitution of the 2'-O atom with alkyl (e.g. 2'-O-methyl), alkynyl (2'-O-alkynyl), alkenyl (2'-O-alkenyl), alkoxyalkyl (e.g. methoxyethyl, 2'-MOE) groups, having a length as specified above, and the like. In addition, the phosphodiester group of the backbone may be modified by thioation, dithioation, amidation and the like to yield phosphorothioate, phosphorodithioate, phosphoramidate, etc., internucleosidic linkages. The internucleosidic linkages may be replaced in full or in part by peptidic linkages to yield in peptidonucleic acid sequences and the like. Alternatively, or in addition, the nucleobases may be modified by (de)amination, to yield inosine or 2'6'-diaminopurines and the like. A further modification may be methylation of the C5 in the cytidine moiety of the nucleotide, to reduce potential immunogenic properties known to be associated with CpG sequences.

In case the dsRNA complex recruits ADAR enzymes to deaminate an A to I in the target RNA sequence, the base-pair, mismatch, bulge or wobble between the adenosine to be edited and the opposite nucleotide may comprise an adenosine, a guanine, an uridine or a cytidine residue, but preferably a cytidine residue. Except for the potential mismatch opposite the editing site (when no uridine is applied), the remaining portion of the AON may be perfectly complementary to the target RNA. However, as shown herein, in certain aspects the invention relates to AONs that comprise a limited number of imperfect matches. It will be understood by a person having ordinary skill in the art that the extent to which the editing entities inside the cell are redirected to other target sites may be regulated by varying the affinity of the oligonucleotides according to the invention for the recognition domain of the editing molecule. The exact modification may be determined through some trial and error and/or through computational methods based on structural interactions between the oligonucleotide and the recognition domain of the editing molecule.

In addition, or alternatively, the degree of recruiting and redirecting the editing entity resident in the cell may be regulated by the dosing and the dosing regimen of the oligonucleotide. This is something to be determined by the experimenter (in vitro) or the clinician, usually in phase I and/or II clinical trials.

The invention concerns the modification of target RNA sequences in eukaryotic, preferably metazoan, more preferably mammalian cells. In principle the invention can be used with cells from any mammalian species, but it is preferably used with a human cell. The invention can be used with cells from any organ e.g. skin, lung, heart, kidney, liver, pancreas, gut, muscle, gland, eye, brain, blood and the like. The invention is particularly suitable for modifying sequences in cells, tissues or organs implicated in a diseased state of a (human) subject. Such cells include but are not limited to epithelial cells of the lung or the gastrointestinal tract, cells of the reproductive organs, muscle cells, cells of the eye, cells of the skin, cells from tissues and organs such as liver, kidney, pancreas, immune cells, cancerous cells, gland cells, brain cells, and the like. The invention can also be used with mammalian cells which are not naturally present in an organism e.g. with a cell line or with an embryonic stem (ES) cell. The invention can be used with various types of stem cell, including pluripotent stem cells, totipotent stem cells, embryonic stem cells, induced pluripotent stem cells, etc. The cell can be located in vitro or in vivo. One advantage of the invention is that it can be used with cells in situ in a living organism, but it can also be used with cells in culture. In some embodiments cells are treated ex vivo and are then introduced into a living organism (e.g. reintroduced into an organism from whom they were originally derived). The invention can also be used to edit target RNA sequences in cells within a so-called organoid. Organoids can be thought of as three-dimensional in vitro-derived tissues but are driven using specific conditions to generate individual, isolated tissues (e.g. see Lancaster & Knoblich, Science 2014, vol. 345 no. 6194 1247125). In a therapeutic setting they are useful because they can be derived in vitro from a patient's cells, and the organoids can then be reintroduced to the patient as autologous material which is less likely to be rejected than a normal transplant. Thus, according to another preferred embodiment, the invention may be practised on organoids grown from tissue samples taken from a patient (e.g. from their gastrointestinal tract; see Sala et al. J Surg Res. 2009; 156(2):205-12, and also Sato et al. Gastroenterology 2011; 141:1762-72); upon RNA editing in accordance with the invention, the organoids, or stem cells residing within the organoids, may be used to transplant back into the patient to ameliorate organ function. The cell to be treated will generally have a genetic mutation. The mutation may be heterozygous or homozygous. The invention will typically be used to modify point mutations, such as N to A mutations, wherein N may be G, C, U (on the DNA level T), preferably G to A mutations, or N to C mutations, wherein N may be A, G, U (on the DNA level T), preferably U to C mutations. Genes containing mutations of particular interest are discussed below. In some embodiments, however, the invention is used in the opposite way by introducing a disease-associated mutation into a cell line or an animal, in order to provide a useful research tool for the disease in question. As an example of creating a disease model, we have provided an oligonucleotide sequence that provides for the recruitment of editing activity in a human cell to create a mutation in the CEP290 gene, creating a cryptic splice site that forms the basis for a form of Leber's Congenital Amaurosis (LCA 10), the most common form of congenital child blindness.

A mutation to be reverted through RNA editing may have arisen on the level of the chromosome or some other form of DNA, such as mitochondrial DNA, or RNA, including pre-mRNA, ribosomal RNA or mitochondrial RNA. A change to be made may be in a target RNA of a pathogen, including fungi, yeasts, parasites, kinetoplastids, bacteria, phages, viruses etc, with which the cell or subject has been infected. Subsequently, the editing may take place on the RNA level on a target sequence inside such cell, subject or pathogen. Certain pathogens, such as viruses, release their nucleic acid, DNA or RNA into the cell of the infected host (cell). Other pathogens reside or circulate in the infected host. The oligonucleotide constructs of the invention may be used to edit target RNA sequences residing in a cell of the infected eukaryotic host, or to edit a RNA sequence inside the cell of a pathogen residing or circulating in the eukaryotic host, as long as the cells where the editing is to take place contain an editing entity compatible with the oligonucleotide construct administered thereto.

Without wishing to be bound be theory, the RNA editing through hADAR1 and hADAR2 is thought to take place on primary transcripts in the nucleus, during transcription or splicing, or in the cytoplasm, where e.g. mature mRNA, miRNA or ncRNA can be edited. Different isoforms of the editing enzymes are known to localize differentially, e.g. with hADAR1 p110 found mostly in the nucleus, and hADAR1 p150 in the cytoplasm. The RNA editing by cytidine deaminases is thought to take place on the mRNA level. Editing of mitochondrial RNA codons or non-coding sequences in mature mRNAs is not excluded.

The invention is used to make a change in a target RNA sequence in a eukaryotic cell through the use of an oligonucleotide that is capable of targeting a site to be edited and recruiting RNA editing entities resident in the cell to bring about the editing reaction(s). Preferred editing reactions are adenosine deaminations and cytidine deaminations, converting adenosines into inosines and cytidines into uridines, respectively. The changes may be in 5' or 3' untranslated regions of a target RNA, in (cryptic) splice sites, in exons (changing amino acids in protein translated from the target RNA, codon usage or splicing behaviour by changing exonic splicing silencers or enhancers, by introducing or removing start or stop codons), in introns (changing splicing by altering intronic splicing silencers or intronic splicing enhancers, branch points) and in general in any region affecting RNA stability, structure or functioning. The target RNA sequence may comprise a mutation that one may wish to correct or alter, such as a point mutation (a transition or a transversion). Alternatively, the target RNA sequence is deliberately mutated to create an altered phenotype (or genotype, in case of RNA based organisms, such as RNA viruses), where there was no mutation before. For example cell lines or animals may be made which carry changes (mutations) in a target RNA sequence, which may be used in assays or as (animal, organoid, etcetera) model systems to study disease, test experimental compounds against disease, and the like. The oligonucleotide constructs and methods according to the invention may be used in high throughput screening systems (in arrayed format) for making cell banks with a large variety of target RNAs, for example coding for a large variety of protein isoforms, for further experimentation, including compound screening, protein engineering and the like.

The target RNA may be any cellular or viral RNA sequence, but is more usually a pre-mRNA or an mRNA with a protein coding function.

Purely for ease of reference, and without the intention to limit the invention, the Table 1 is provided to illustrate the potential codon changes that can be brought about by adenosine deaminase editing directed by oligonucleotides of the invention. Table 1 particularly should not be interpreted as a limitation of the applicability of the invention to coding sequences in any RNA; as pointed out already, the invention can be practised on any RNA target comprising an adenosine, whether in a coding region, an intron, a non-coding exon (such as a 5'- or 3' untranslated region), in miRNAs, tRNAs, rRNAs and so on. To avoid any misunderstanding about the width of the applicability, changes that are inconsequential ('silent') from a coding perspective may still alter gene expression of a certain protein as some codons for the same amino acid may be more preferred than others and may lead, for instance, to different transcription stability or translation efficiency, causing the encoded protein to become more or less abundant than without the change.

TABLE 1

| Target codon | Amino acid | Corrected codon | Amino acid |
|---|---|---|---|
| AAA | Lys | GAA | Glu |
|  |  | AGA | Arg |
|  |  | AAG | Lys |
|  |  | GGA | Gly |
|  |  | AGG | Arg |
|  |  | GAG | Glu |
|  |  | GGG | Gly |
| AAC | Asn | GAC | Asp |
|  |  | AGC | Ser |
|  |  | GGC | Gly |
| AAG | Lys | GAG | Glu |
|  |  | AGG | Arg |
|  |  | GGG | Gly |
| AAU | Arg | GAU | Asp |
|  |  | AGU | Ser |
|  |  | GGU | Gly |
| ACA | Thr | GCA | Ala |
|  |  | ACG | Thr |
|  |  | GCG | Ala |
| ACC | Thr | GCC | Ala |
| ACG | Thr | GCG | Ala |
| ACU | Thr | GCU | Ala |
| AGA | Arg | GGA | Gly |
|  |  | AGG | Arg |
|  |  | GGG | Gly |
| AGC | Ser | GGC | Gly |
| AGG | Arg | GGG | Gly |
| AGU | Ser | GGU | Gly |
| AUA | Ile | GAU | Asp |
|  |  | AUG | Met |
|  |  | GUG | Val |
| AUC | Ile | GUC | Val |
| AUG | Met | GUG | Val |

TABLE 1-continued

| Target codon | Amino acid | Corrected codon | Amino acid |
|---|---|---|---|
| AUU | Ile | GUU | Val |
| CAA | Gln | CGA | Arg |
|  |  | CAG | Gln |
|  |  | CGG | Arg |
| CAC | His | CGC | Arg |
| CAG | Gln | CGG | Arg |
| CAU | His | CGU | Arg |
| CCA | Pro | CCG | Pro |
| CGA | Arg | CGG | Arg |
| CUA | Leu | CUG | Leu |
| GAA | Glu | GGA | Gly |
|  |  | GAG | Glu |
|  |  | GGG | Gly |
| GCA | Ala | GCG | Ala |
| GUA | Val | GUG | Val |
| GGA | Gly | GGG | Gly |
| GAC | Asp | GGC | Gly |
| GAG | Glu | GGG | Gly |
| GAU | Asp | GGU | Gly |
| UAA | Stop | UGA | Stop |
|  |  | UAG | Stop |
|  |  | UGG | Trp |
| UCA | Ser | UCG | Ser |
| UGA | Stop | UGG | Trp |
| UUA | Leu | UUG | Leu |
| UAC | Tyr | UGC | Cys |
| UAG | Stop | UGG | Trp |
| UAU | Tyr | UGU | Cys |

Particularly interesting target adenosines for editing using oligonucleotides according to the invention are those that are part of codons for amino acid residues that define key functions, or characteristics, such as catalytic sites, binding sites for other proteins, binding by substrates, localization domains, for co- or post-translational modification, such as glycosylation, hydroxylation, myristoylation, protein cleavage by proteases (to mature the protein and/or as part of the intracellular routing), and so forth.

A host of genetic diseases are caused by G to A mutations, and these are preferred target diseases because adenosine deamination at the mutated target adenosine will reverse the mutation to wild-type. However, reversal to wild-type may not always be necessary to obtain a beneficial effect. Modification of an A to G in a target may also be beneficial if the wild-type nucleotide is other than a G. In certain circumstances this may be predicted to be the case, in others this may require some testing. In certain circumstances, the modification from an A in a target RNA to G where the wild-type is not a G may be silent (not translated into a different amino acid), or otherwise non-consequential (for example an amino acid is substituted but it constitutes a conservative substitution that does not disrupt protein structure and function), or the amino acid is part of a functional domain that has a certain robustness for change. If the A to G transition brought about by editing in accordance with the invention is in a non-coding RNA, or a non-coding part of an RNA, the consequence may also be inconsequential or less severe than the original mutation. Those of ordinary skill in the art will understand that the applicability of the current invention is very wide and is not even limited to preventing or treating disease. The invention may also be used to modify transcripts to study the effect thereof, even if, or particularly when, such modification induces a diseased state, for example in a cell or a non-human animal model. Preferred examples of genetic diseases that can be prevented and/or treated with oligonucleotides according to the invention are any disease where the modification of one or more adenosines in a target RNA will bring about a (potentially) beneficial change.

Transcribed RNA sequences that are potential target RNA sequences according to the invention, containing mutations of particular interest include, but are not limited to those transcribed from the CFTR gene (the cystic fibrosis transmembrane conductance regulator), dystrophin, huntingtin, neurofibromin 2, neurofibromin 2, the β-globin chain of haemoglobin, CEP290 (centrosomal protein 290 kDa), the HEXA gene of the β-hexosaminidase A, and any one of the Usher genes (e.g. USH2A encoding Usherin) responsible for a form of genetic blindness called Usher syndrome. A more extensive list is presented further below. The target sequence will be selected accordingly, and the oligonucleotide construct will include the desired modification in order to correct the mutation. Those skilled in the art of CF mutations recognise that between 1000 and 2000 mutations are known in the CFTR gene, including R117H, G542X, G551D, R553X, W1282X, and N1303K.

In general, mutations in any target RNA that can be reversed using oligonucleotide constructs according to the invention are G to A mutations, in the case of adenosine deaminase recruitment, and U to C mutations in the case of cytidine deaminase recruitment, and oligonucleotide constructs can be designed accordingly. Mutations that may be targeted using oligonucleotide constructs according to the invention also include C to A, U to A (T to A on the DNA level) in the case of recruiting adenosine deaminases, and A to C and G to C mutations in the case of recruiting cytidine deaminases. Although RNA editing in the latter circumstances may not necessarily revert the mutation to wild-type, the edited nucleotide may give rise to an improvement over the original mutation. For example, a mutation that causes an in frame stop codon—giving rise to a truncated protein, upon translation—may be changed into a codon coding for an amino acid that may not be the original amino acid in that position, but that gives rise to a (full length) protein with at least some functionality, at least more functionality than the truncated protein. The target sequence is endogenous to the eukaryotic, preferably mammalian, more preferably human cell. Thus the target sequence is not, for instance, a transgene or a marker gene which has been artificially introduced at some point in the cell's history, but rather is a gene that is naturally present in the cell (whether in mutant or non-mutant form).

The invention is not limited to correcting mutations, as it may instead be useful to change a wild-type sequence into a mutated sequence by applying oligonucleotides according to the invention. One example where it may be advantageous to modify a wild-type adenosine is to bring about skipping of an exon, for example by modifying an adenosine that happens to be a branch site required for splicing of said exon. Another example is where the adenosine defines or is part of a recognition sequence for protein binding, or is involved in secondary structure defining the stability of the mRNA. As noted above, therefore, the invention can be used to provide research tools for diseases, to introduce new mutations which are less deleterious than an existing mutation, etc. The amount of oligonucleotide to be administered, the dosage and the dosing regimen can vary from cell type to cell type, the disease to be treated, the target population, the mode of administration (e.g. systemic versus local), the severity of disease and the acceptable level of side activity, but these can and should be assessed by trial and error during in vitro research, in pre-clinical and clinical trials. The trials are particularly straightforward when the modified sequence leads to an easily-detected phenotypic change. It is possible that higher doses of oligonucleotide could compete for binding to a nucleic acid editing entity (e.g. ADAR) within a cell, thereby depleting the amount of the entity which is free to take part in RNA editing, but routine dosing trials will reveal any such effects for a given oligonucleotide and a given target.

One suitable trial technique involves delivering the oligonucleotide construct to cell lines, or a test organism and then taking biopsy samples at various time points thereafter. The sequence of the target RNA can be assessed in the biopsy sample and the proportion of cells having the modification can easily be followed. After this trial has been performed once then the knowledge can be retained and future delivery can be performed without needing to take biopsy samples. A method of the invention can thus include a step of identifying the presence of the desired change in the cell's target RNA sequence, thereby verifying that the target RNA sequence has been modified. This step will typically involve sequencing of the relevant part of the target RNA, or a cDNA copy thereof (or a cDNA copy of a splicing product thereof, in case the target RNA is a pre-mRNA), as discussed above, and the sequence change can thus be easily verified. Alternatively the change may be assessed on the level of the protein (length, glycosylation, function or the like), or by some functional read-out, such as a(n) (inducible) current, when the protein encoded by the target RNA sequence is an ion channel, for example. In the case of CFTR function, an Using chamber assay or an NPD test in a mammal, including humans, are well known to a person skilled in the art to assess restoration or gain of function.

After RNA editing has occurred in a cell, the modified RNA can become diluted over time, for example due to cell division, limited half-life of the edited RNAs, etc. Thus, in practical therapeutic terms a method of the invention may involve repeated delivery of an oligonucleotide construct until enough target RNAs have been modified to provide a tangible benefit to the patient and/or to maintain the benefits over time.

Oligonucleotides of the invention are particularly suitable for therapeutic use, and so the invention provides a pharmaceutical composition comprising an oligonucleotide of the invention and a pharmaceutically acceptable carrier. In some embodiments of the invention the pharmaceutically acceptable carrier can simply be a saline solution. This can usefully be isotonic or hypotonic, particularly for pulmonary delivery. The invention also provides a delivery device (e.g. syringe, inhaler, nebuliser) which includes a pharmaceutical composition of the invention.

The invention also provides an oligonucleotide of the invention for use in a method for making a change in a target RNA sequence in a mammalian, preferably human cell, as described herein. Similarly, the invention provides the use of an oligonucleotide construct of the invention in the manufacture of a medicament for making a change in a target RNA sequence in a mammalian, preferably human cell, as described herein.

The invention also relates to a method for the deamination of at least one specific target adenosine present in a target RNA sequence in a cell, said method comprising the steps of: providing said cell with an AON according to the invention; allowing uptake by the cell of said AON; allowing annealing of said AON to the target RNA sequence; allowing a mammalian ADAR enzyme comprising a natural dsRNA binding domain as found in the wild type enzyme to deaminate said target adenosine in said target RNA sequence to an inosine; and optionally identifying the presence of said inosine in the RNA sequence. Introduction of the AON according to the present invention into the cell is performed by general methods known to the person skilled in the art. After deamination the read-out of the effect (alteration of the target RNA sequence) can be monitored through different ways. Hence, the identification step of whether the desired deamination of the target adenosine has indeed taken place depends generally on the position of the target adenosine in the target RNA sequence, and the effect that is incurred by the presence of the adenosine (point mutation, early stop codon, aberrant splice site, alternative splice site, misfolding of the resulting protein, etc.). Hence, in a preferred aspect, depending on the ultimate deamination effect of A to I conversion, the identification step comprises: sequencing the target RNA; assessing the presence of a functional, elongated, full length and/or wild type protein when said target adenosine is located in a UGA or UAG stop codon, which is edited to a UGG codon through said deamination; assessing the presence of a functional, elongated, full length and/or wild type protein when two target adenosines are located in a UAA stop codon, which is edited to a UGG codon through the deamination of both target adenosines; assessing whether splicing of the pre-mRNA was altered by said deamination; or using a functional read-out, wherein the target RNA after said deamination encodes a functional, full length, elongated and/or wild type protein. In the event that there is a UAA stop codon it means that both adenosines need to be deaminated. Hence, the invention also relates to oligonucleotides and methods wherein two adenosines that are next to each other are co-deaminated by an RNA editing enzyme such as ADAR. In this particular case, the UAA stop codon is converted into a UGG Trp-encoding codon (see Table 1).

Because the deamination of the adenosine to an inosine may result in a protein that is no longer suffering from the mutated A at the target position, the identification of the deamination into inosine may also be a functional read-out, for instance an assessment on whether a functional protein is present, or even the assessment that a disease that is caused by the presence of the adenosine is (partly) reversed. The functional assessment for each of the diseases mentioned herein will generally be according to methods known to the skilled person. When the presence of a target adenosine causes aberrant splicing, the read-out may be the assessment of whether the aberrant splicing is still taking place, or not, or less. On the other hand, when the deamination of a target adenosine is wanted to introduce a splice site, then similar approaches can be used to check whether the required type of splicing is indeed taking place. A very suitable manner to identify the presence of an inosine after deamination of the target adenosine is of course RT-PCR and sequencing, using methods that are well-known to the person skilled in the art.

The oligonucleotide according to the invention is suitably administrated in aqueous solution, e.g. saline, or in suspension, optionally comprising additives, excipients and other ingredients, compatible with pharmaceutical use, at concentrations ranging from 1 ng/ml to 1 g/ml, preferably from 10 ng/ml to 500 mg/ml, more preferably from 100 ng/ml to 100 mg/ml. Dosage may suitably range from between about 1 µg/kg to about 100 mg/kg, preferably from about 10 µg/kg to about 10 mg/kg, more preferably from about 100 µg/kg to about 1 mg/kg. Administration may be by inhalation (e.g. through nebulization), intranasally, orally, by injection or infusion, intravenously, subcutaneously, intra-dermally, intra-cranially, intramuscularly, intra-tracheally, intra-peritoneally, intra-rectally, by direct injection into a tumor, and the like. Administration may be in solid form, in the form of a powder, a pill, or in any other form compatible with pharmaceutical use in humans. The invention is particularly suitable for treating genetic diseases, such as cystic fibrosis, albinism, alpha-1-antitrypsin (A1AT) deficiency, Alzheimer disease, Amyotrophic lateral sclerosis, Asthma, ß-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermylosis bullosa, Fabry disease, Factor V Leiden associated disorders, Familial Adenomatous, Polyposis, Galactosemia, Gaucher's Disease, Glucose-6-phosphate dehydrogenase, Haemophilia, Hereditary Hematochromatosis, Hunter Syndrome, Huntington's disease, Hurler Syndrome, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-esol related cancer, Parkinson's disease, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, various forms of cancer (e.g. BRCA1 and 2 linked breast cancer and ovarian cancer), and the like.

In some embodiments the oligonucleotide construct can be delivered systemically, but it is more typical to deliver an oligonucleotide to cells in which the target sequence's phenotype is seen. For instance, mutations in CFTR cause cystic fibrosis which is primarily seen in lung epithelial tissue, so with a CFTR target sequence it is preferred to deliver the oligonucleotide construct specifically and directly to the lungs. This can be conveniently achieved by inhalation e.g. of a powder or aerosol, typically via the use of a nebuliser. Especially preferred are nebulizers that use a so-called vibrating mesh, including the PARI eFlow (Rapid) or the i-neb from Respironics. The inventors have found that inhaled use of oligonucleotide constructs can lead to systemic distribution of the oligonucleotide construct and uptake by cells in the gut, liver, pancreas, kidney and salivary gland tissues, among others. It is therefore to be expected that inhaled delivery of oligonucleotide constructs according to the invention can also target these cells efficiently, which in the case of CFTR gene targeting could lead to amelioration of gastrointestinal symptoms also associated with cystic fibrosis. For other target sequences, depending on the disease and/or the target organ, administration may be topical (e.g. on the skin), intradermal, subcutaneous, intramuscular, intravenous, oral, ocular injection, etc.

In some diseases the mucus layer shows an increased thickness, leading to a decreased absorption of medicines via the lung. One such a disease is chronical bronchitis, another example is cystic fibrosis. Various forms of mucus normalizers are available, such as DNases, hypertonic saline or mannitol, which is commercially available under the name of Bronchitol. When mucus normalizers are used in combination with RNA editing oligonucleotide constructs, such as the oligonucleotide constructs according to the invention, they might increase the effectiveness of those medicines. Accordingly, administration of an oligonucleotide construct according to the invention to a subject, preferably a human subject is preferably combined with mucus normalizers, preferably those mucus normalizers described herein. In addition, administration of the oligonucleotide constructs according to the invention can be combined with administration of small molecule for treatment of CF, such as potentiator compounds for example Kalydeco (ivacaftor; VX-770), or corrector compounds, for example VX-809 (lumacaftor) and/or VX-661. Other combination therapies in CF may comprise the use of an oligonucleotide construct according to the invention in combination with an inducer of adenosine deaminase, using IFN-gamma or TNF-alpha.

Alternatively, or in combination with the mucus normalizers, delivery in mucus penetrating particles or nanoparticles can be applied for efficient delivery of RNA editing molecules to epithelial cells of for example lung and intestine. Accordingly, administration of an oligonucleotide construct according to the invention to a subject, preferably a human subject, preferably uses delivery in mucus penetrating particles or nanoparticles.

Chronic and acute lung infections are often present in patients with diseases such as cystic fibrosis. Antibiotic treatments reduce bacterial infections and the symptoms of those such as mucus thickening and/or biofilm formation. The use of antibiotics in combination with oligonucleotide constructs according to the invention could increase effectiveness of the RNA editing due to easier access of the target cells for the oligonucleotide construct. Accordingly, administration of an oligonucleotide construct according to the invention to a subject, preferably a human subject, is preferably combined with antibiotic treatment to reduce bacterial infections and the symptoms of those such as mucus thickening and/or biofilm formation. The antibiotics can be administered systemically or locally or both.

For application in for example cystic fibrosis patients the oligonucleotide constructs according to the invention, or packaged or complexed oligonucleotide constructs according to the invention may be combined with any mucus normalizer such as a DNase, mannitol, hypertonic saline and/or antibiotics and/or a small molecule for treatment of CF, such as potentiator compounds for example ivacaftor, or corrector compounds, for example lumacaftor and/or VX-661. To increase access to the target cells, Broncheo-Alveolar Lavage (BAL) could be applied to clean the lungs before administration of the oligonucleotide according to the invention.

EXAMPLES

Example 1: Editing of a Non-Sense Mutation in GFP Target RNA Using Different Antisense Oligonucleotides and Sequence Analysis RNA editing was first investigated in a cell system using HeLa cells that contain an expression construct encoding a Green Fluorescent Protein (GFP), stably integrated into the cellular genome. In this construct, a stop codon (TAG) has been introduced at codon position 57, resulting in a triplet UAG in the mRNA. Editing of the RNA at the adenosine in the middle of this triplet would eventually result in the expression of a normal full length protein. The construct (see below) and the cell line were generated using techniques known to the person of ordinary skill in the art.

It was investigated whether the middle A in this triplet could in fact be deaminated to an I (which would subsequently be read as a G), using a set of different antisense oligonucleotides comprising different mismatches in comparison to the target RNA, see FIG. 1. Editing of the UAG triplet would result in a UGG, representing a Trp codon, and subsequently functional GFP protein. To ensure that no other adenosines in the target RNA would be edited, only the three nucleotides in the antisense oligonucleotide opposite the stop codon (the 3'-ACC-5' in each of the oligonucleotides, with the mismatched C in the middle, see FIG. 1) did not contain a 2'-OMe group, whereas all other nucleotides in the antisense oligonucleotide did. Furthermore, the terminal four linkages on each side of all tested oligonucleotides are phosphorothioate linkages, whereas the remaining linkages were normal phosphodiester linkages.

As a first step, it was investigated whether sequence analysis would reveal that the nucleotide at that position could indeed be edited by a combination of any of the oligonucleotides of the present invention and ADAR2. For this, 0.4×10⁶ HeLa cells stably expressing the GFPstop57 construct were seeded per well (6-well plates) in Dulbecco's modified Eagle's medium with 10% fetal bovine serum. After 24 h, cells for subsequent AON transfections were transfected with 2 µg ADAR2 overexpression plasmid (RC212324; Origene) using Lipofectamine 3000. 48 h later selected cell samples were transfected with either 0, 50, or 100 nM of each AON (see FIG. 1) using Lipofectamine 3000. After another 24 h, RNA was isolated from lysed cells and used as a template for cDNA synthesis. Analysis of RNA editing was performed by RT-PCR (forward primer 5'-AGAGGGTGAAGGTGATGCAA-3' (SEQ ID NO:7) and reverse primer 5'-GGGCATGGCACTCTTGAAAA-3' (SEQ ID NO:8)), followed by Sanger sequencing of the PCR product, using general RT-PCR and sequencing methods known to the person skilled in the art. The efficiency of A-to-I editing can be analyzed by Sanger sequencing of the RT-PCR products, where A-to-I editing should be apparent in the sequencing chromatogram as (a partial) shift in the intensity of the signal from A to G. While the method is not fully quantitative, the ratio of the A and G frequencies can be used as an approximate estimation of the A-to-I editing efficiency. As expected, no signal for G is observed overlapping the A peak at the target site in samples that were not transfected with any AON (FIG. 2, panels A and B). In contrast, in samples transfected with AONs a partial change into a G is observed at this position, as indicated by the overlapping A and G peaks (green and black in FIG. 2, respectively). The effect is variable: while a small amount of overlapping G signal at the target site can be observed with each AON, the effect is strongest with AONs ADAR58 and ADAR59 (FIG. 2 G-J).

Wobble base pairs play a fundamental role in RNA secondary structure and are present in tRNAs in large extend. Very often their occurrences in the RNA sequences are close to bulged RNA structures, loops and mismatches. To investigate the effect of the presence of wobble base pairs in the AON on RNA editing the inventors of the present invention designed ADAR72-1 containing five wobble base pairs. Its ability to induce editing of the non-sense mutation in GFP target RNA (see above) was investigated and compared to oligonucleotide ADAR59-2 (=ADAR59, see above), which has the exact same sequence but without wobble base pairs:

```
(ADAR59-2)
3'-GAUGGACAAGGUACCGGUUGUGAAGAGUCAUGAAAGAGAAUAGAAGAAGUUAC-5'
5'-AACUACCUGUUCCAUAGCCAACACUUGUCACUACUUUCUCUUAUGGUGUUCAAUGCU-3'

(ADAR72-1)
3'-GAUGGACGAGGUACCGGUUGUGGAGAGUCGUGAAAGAGAAUGGAAGGAGUUAC-5'
5'-AACUACCUGUUCCAUAGCCAACACUUGUCACUACUUUCUCUUAUGGUGUUCAAUGCU-3'
       ↑              ↑       ↑         ↑      ↑
```

The upper strand is the AON, whereas the lower strand is the 5' to 3' target RNA. The targeted adenosine is in bold. Mismatches and wobbles are underlined and the arrows show the positions of additional wobble base pairs.

ADAR59-2 (=ADAR59; SEQ ID NO:4, see also Example 5) and ADAR72-1 (SEQ ID NO:34) are chemically modified as shown below: lower case represents 2'-O-methyl modified RNA nucleotides, whereas the upper case nucleotides are unmodified RNA nucleotides. The asterisks represent the internucleoside phosphorothioate linkages at the 3' and 5' ends of the AONs. Mismatches and wobbles are indicated by underlining.

ADAR59-2
5'-c*a*u*u*gaagaagauaagagaaaguacugagaaguguuggCCAug
gaacag*g*u*a*g-3'

ADAR72-1
5'-c*a*u*u*gaggaagguaagagaaagugcugagagguguuggCCAug
gagcag*g*u*a*g-3'

Figure 3:
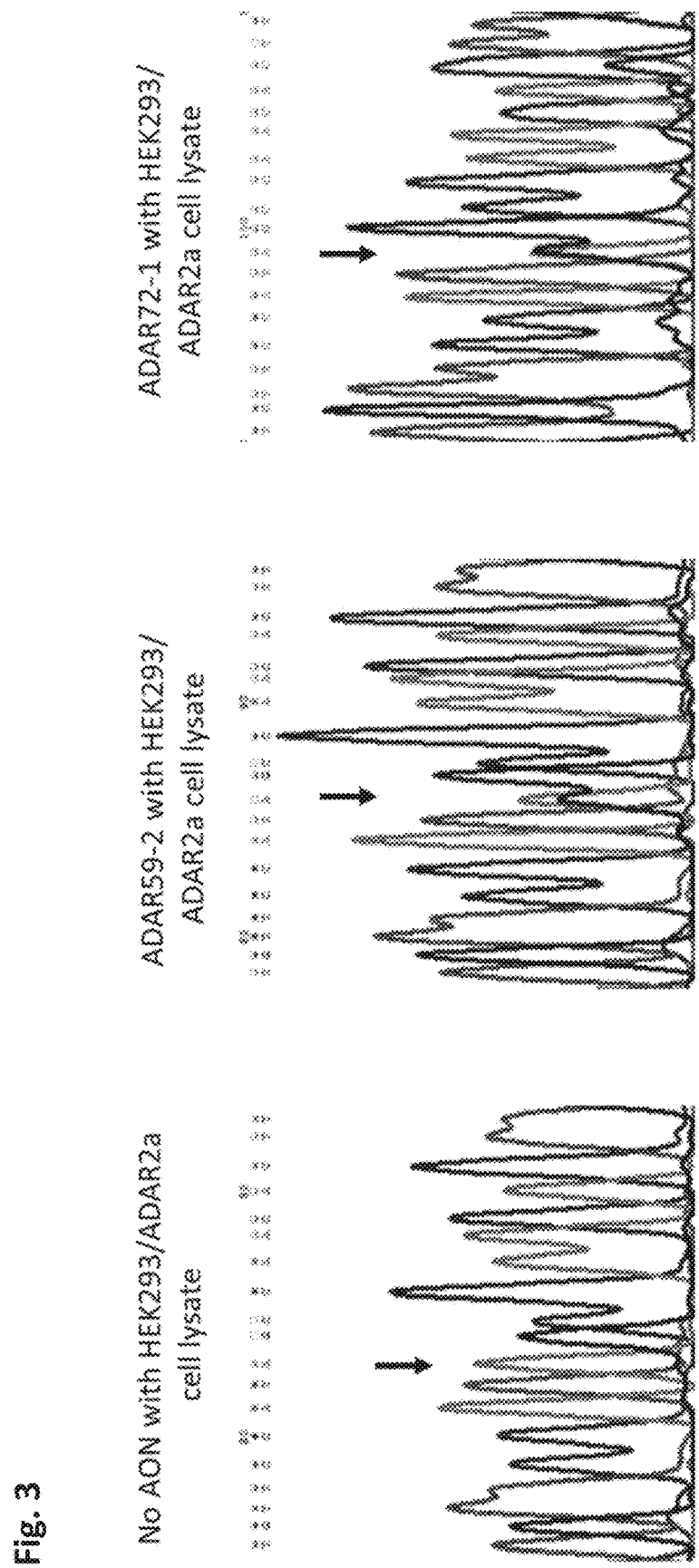
FIG. 3 shows the sequencing results after use of ADAR59-2 and ADAR72-1 (that in comparison to ADAR59-2 contains additional wobble base pairs) in a HeLa cell lysate from cells transfected with ADAR2a on the GFP target sequence. The additional wobbles add to the RNA editing efficiency. The position of the edited target is given by an arrow.

Both ADAR59-2 and ADAR72-1 were tested in an in vitro editing assay using HEK293 cell lysates with overexpressed isoform 2 of ADAR2 (ADAR2a). HEK293 cell lysate with overexpressed ADAR2a but without AON were used as negative controls. To obtain the lysates, HEK293 cells were first transfected overnight with 500 ng ADARB1 expression plasmid (OriGene) using Lipofectamine 3000. Cells were then lysed using Lysis-M reagent. 200 nM AONs and 90 nM template ssRNA were pre-incubated together in an in vitro editing assay buffer for 30 min at 30° C. After pre-incubation the cell lysates were added (10 μl) and the reaction mix was incubated for 30 min at 30° C. and subsequently for 30 min at 37° C. Targeted RNAs were then extracted by phenol chloroform extraction and reverse transcribed using Maxima RT Reagents, using the protocol of the manufacturer, and sequencing was prepared as described above. The sequencing data provided in FIG. 3 show no detectable A-to-I editing for the sample where no AON was used: no G signal above background was seen. In contrast, there is a clear presence of the G signal visible for the sample where oligonucleotide ADAR59-2 was used in the editing assay. Additionally even higher intensity of the G signal is shown for oligonucleotide ADAR72-1 indicating that presence of the additional wobble base pairs in the target RNA/AON sequence helps to increase the A-to-I editing.

Example 2. RNA Editing in the Treatment of Hurler Syndrome

One potential disease target for RNA editing using the system of the present invention is mucopolysaccharidosis type I-Hurler (MPS I-H; Hurler syndrome). This disease is caused by a c.1205G>A (W402X) mutation in the IDUA gene, which encodes the lysosomal enzyme α-L-iduronidase. Editing the A to I using the methods and means of the present invention would potentially reverse the mutation to a wild type sequence. Hurler syndrome is a lysosomal storage disorder, which causes multiple organ failure due to accumulation of glycosaminoglycans. A mouse model with a similar mutation (W392X) exists, with the mutation in the endogenous gene. Initial experiments are performed in this mouse model, assessing the effect in different tissues and organs. Furthermore, the level of glycosaminoglycans in different tissues is assessed to evaluate the therapeutic potential of the editing approach.

Part of the sequence of exon 9 of the mouse Idua gene is as follows (mutation in bold):

5'-ATGGAGAACAACTCTAGGCAGAGGTCTCAAAGGCTGGGGCTGTGTTG

GACAGCAATCATACAGTGGGT-3'

This DNA sequence is SEQ ID NO:11, the corresponding RNA sequence is SEQ ID NO:12. The inventors of the present invention generated a number of antisense oligonucleotides directed towards the pre-mRNA coming from this part of the Idua sequence that are used in RNA editing as outlined herein using the mouse model, with the following sequences (upper strand is the 3' to 5' oligonucleotide; lower strand is the 5' to 3' target RNA (SEQ ID NO:12); mismatches and wobbles are underlined):

3'-CCUCUUGUUGAGAC̲CCGUCUCCAGAGUUUCCGACCCCGACACAACCU

GUC-5' (ADAR65)

5'-AUGGAGAACAACUCUAGGCAGAGGUCUCAAAGGCUGGGGCUGUGUUG

GACAGCAAUCAUACAGUGGGU-3'

3'-CCUCUUGUUGAGAC̲CCGUCUCCAGAGUUUCCGACCCCGACACAACCU

GUC-5' (ADAR65-2)

5'-AUGGAGAACAACUCUAGGCAGAGGUCUCAAAGGCUGGGGCUGUGUUG

GACAGCAAUCAUACAGUGGGU-3'

3'-CCUCUUGUUGAGAC̲C̲UGUCUCCAGAGUUUCCGACCCCGACACAACCU

GUC-5' (ADAR65-2x)

5'-AUGGAGAACAACUCUAGGCAGAGGUCUCAAAGGCUGGGGCUGUGUUG

GACAGCAAUCAUACAGUGGGU-3'

3'-UUGUUGAGAC̲CCGUCUCCAGAGUUUCCGACCCCGACACAACCUGUC-

5' (ADAR66)

5'-AUGGAGAACAACUCUAGGCAGAGGUCUCAAAGGCUGGGGCUGUGUUG

GACAGCAAUCAUACAGUGGGU-3'

3'-CCUCUUGUUGAGAC̲CCGUCUCCAGAGA̲UUC̲AGACCCCGACA̲ACCCCU

GUC-5' (ADAR67)

5'-AUGGAGAACAACUCUAGGCAGAGGUCUCAAAGGCUGGGGCUGUGUUG

GACAGCAAUCAUACAGUGGGU-3'

3'-CCUCUUGUUGAGAC̲CCGUCUCCAGAGA̲UUC̲AGACC̲UC̲GACA̲ACUCCU

GUCGUUA 5' (ADAR91)

5'-AUGGAGAACAACUCUAGGCAGAGGUCUA̲AAAGGCUGGGGCUGUGUUG

GACAGCAAUCAUACAGUGGGU-3'

3'-CCUCUUGUUGAGAC̲CCGUCUCCAGAGUUUCCGACC̲UC̲GACACA-5'

(ADAR93)

5'-AUGGAGAACAACUCUAGGCAGAGGUCUCAAAGGCUGGGGCUGUGUUG

GACAGCAAUCAUACAGUGGGU-3'

ADAR65 (SEQ ID NO:13), ADAR65-2 (SEQ ID NO:24), ADAR65-2x (SEQ ID NO:25), ADAR66 (SEQ ID NO:14), ADAR67 (SEQ ID NO:15), ADAR91 (SEQ ID NO:26) and ADAR93 (SEQ ID NO:27) have a number of chemical modifications, as follows:

ADAR65:
5'-c*u*g*u*ccaacacagcccagccuuugagaccucugcC̲C̲Agaguu guu*c*u*c*c-3'

ADAR65-2:
5'-c*u*g*u*ccaacacagcccagccuuugagaccucugcc̲agaguu guu*c*u*c*c-3'

ADAR65-2x:
5'-c*u*g*u*ccaacacagcccagccuuugagaccucugu̲C̲C̲Agaguu guu*c*u*c*c-3'

ADAR66:
5'-c*u*g*u*ccaacacagcccagccuuugagaccucugcC̲C̲Agagu* u*g*u*u-3'

ADAR67:
5'-c*u*g*u*cc̲c̲c̲aacagcccagac̲uua̲gagaccucugcC̲C̲Agaguu guu*c*u*c*c-3'

ADAR91:
5'-a*u*u*g*cuguccu̲ca̲acagcu̲ccaga̲cuua̲gagaccucugcC̲C̲Ag aguuguu*c*u*c*c-3'

ADAR93:
5'-a*c*a*c*agcu̲ccagccuuugagaccucugcC̲C̲Agaguuguu*c*u

-continued

```
*c*c-3'
```

Lower case letters represent 2'-O methyl modified RNA nucleotides, the upper case nucleotides are unmodified RNA nucleotides (hence, no 2'-O methyl modification) and surround the center cytidine that is opposite the target adenosine, except in ADAR65-2, which has a 2'-O methyl modification on all its nucleotides. The asterisks depict the (4) phosphorothioate linkages at all termini of the oligonucleotides. Mismatches and wobbles are indicated by underlining. ADAR91 has 5 (regions of) mismatches/wobbles with the target RNA, ADAR67 has 4, ADAR93 and ADAR65-2X both have 2, whereas ADAR65, ADAR65-2 and ADAR66 AONs only differ at the nucleotide opposite the target adenosine. ADAR65 and ADAR66 are identical in modifications but ADAR66 is 2 nucleotides shorter than ADAR65 at the 3' end.

The effect of these AONs on restoring the wild type sequence was tested in an assay that measures the activity of the α-L-iduronidase enzyme encoded by Idua. For this, immortalized embryonic fibroblast cells (70,000 per sample) derived from a W392X mouse were cultured in growth medium (DMEM/10% FCS), and transfected with 1 µg of plasmid expressing the Idua W392X mRNA using Lipofectamine 3000. After 24 h, the cells were similarly transfected with 100 nM (final concentration) of oligonucleotide, and cultured for additional 48 h. Cells were then collected and lysed in mPER buffer (Thermo Scientific #78501). The cell fragments were removed from the lysates by centrifugation and 25 µl of the supernatant was used for the enzymatic assay: 25 µl of 360 µM 4-Methylumbelliferyl α-L-iduronide in 0.4 M sodium formate buffer (pH 3.5) was added in the lysate samples, which were then incubated for 2 h at 37° C. Reaction was terminated by addition of 200 µl of 0.17 M glycine buffer (pH 9.9), and the resulting fluorescent intensity was then measured (excitation wavelength 365 nm and emission 450 nm). Results were normalized to total protein concentration of the samples, as measured by BCA assay (Pierce™ BCA Protein Assay Kit, Thermo Scientific).

Figure 4:
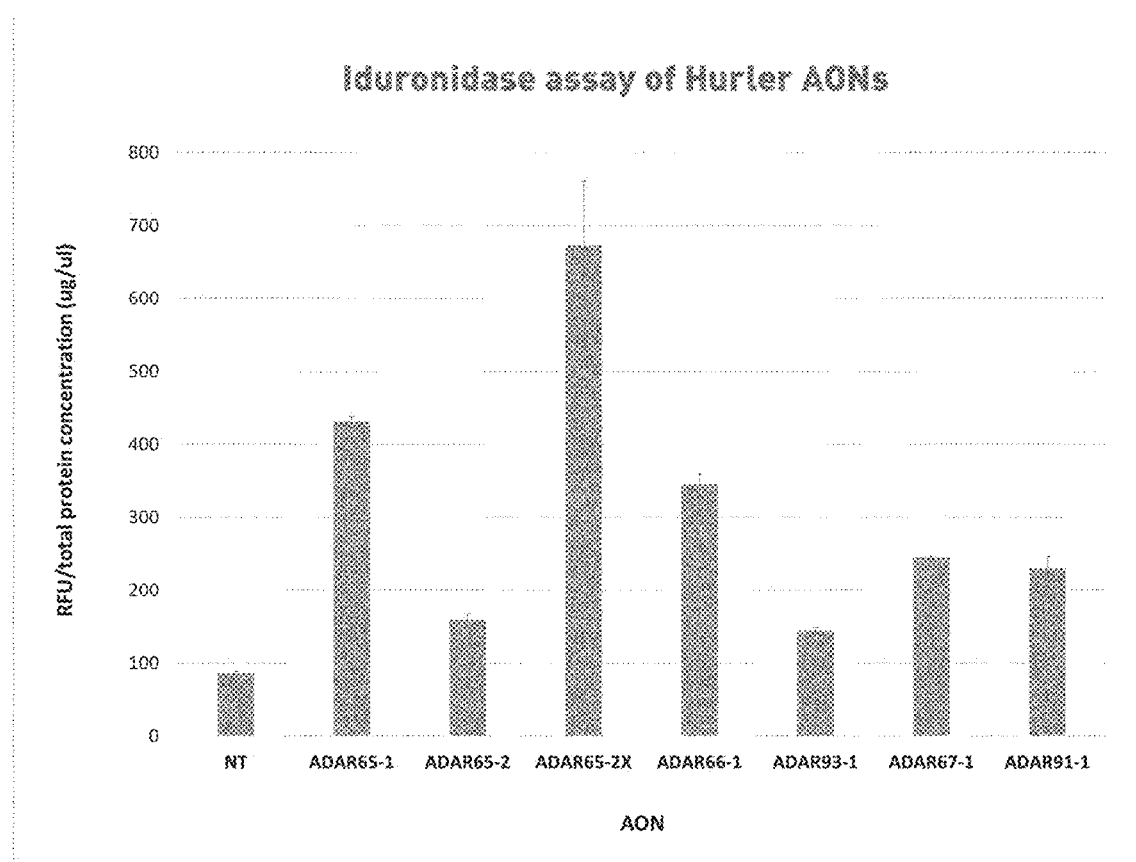
FIG. 4 shows the enzymatic activity (as relative fluorescence units normalized to total protein concentration) measured in the α-L-iduronidase assay. Average activity and standard deviation from two duplicate measurements is shown for each AON, as indicated. NT: Non-treated.

The results (see FIG. 4) clearly indicate that, under these conditions, transfections with oligonucleotides ADAR65-2 and ADAR 93-1 resulted in only small improvements in enzymatic activity (less than 2-fold), as compared to the fluorescence obtained with samples from the non-oligonucleotide-treated cells (NT) that only express the mutant Idua mRNA. In contrast, significant increases were observed with the other AONs, with AONs ADAR67 and ADAR91 resulting in more than 2-fold increase in activity, and AONs ADAR66, ADAR65 and ADAR65-2X resulting in more than 3, 4 and 6-fold increase, respectively.

Subsequently, based on modelling data of the interaction between the oligonucleotide, the target RNA and the ADAR protein, the inventors envisioned that a mismatch of the oligonucleotide with position 4 upstream from the editing site could enhance binding of ADAR proteins to the target RNA, and thereby increase editing efficiency and editing levels. Four oligonucleotides (ADAR93-2, ADAR93-3, ADAR93-4 and ADAR93-5) were designed to test the effect of a mismatch at the position 4 on editing of the target pre-mRNA of the mouse Idua mutated gene (W392X) and restoring its WT sequence.

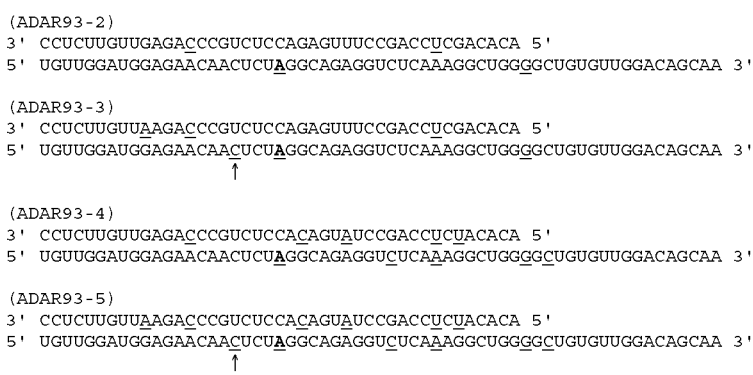

Upper strands are the oligonucleotides, the lower strand is the target RNA with the mutation (A) in bold. Mismatches and wobbles are underlined. The mismatch between oligonucleotide ADAR93-3 and ADAR93-5 with the target sequence at the position that is 4 nucleotides upstream of the mutation in the target sequence is indicated with an arrow. ADAR92-2 is (besides that mismatch) identical to ADAR93-3. ADAR93-4 is (besides that mismatch) identical to ADAR93-5. ADAR93-2 (SEQ ID NO:28), ADAR93-3 (SEQ ID NO:29), ADAR93-4 (SEQ ID NO:30) and ADAR93-5 (SEQ ID NO:31) have a number of chemical modifications, as follows:

Lower case letters represent 2'-O methyl modified RNA nucleotides, the upper case nucleotides are unmodified RNA nucleotides (hence, no 2'-O methyl modification). The asterisks between nucleosides depict phosphorothioate linkages. Mismatches and wobbles are indicated by underlining.

The effect of these four oligonucleotides on restoring the wild type sequence was tested in the editing and enzymatic assay as described above. As shown in FIGS. 5(A) and (B) the introduction of the C-A mismatch of oligonucleotide ADAR93-2 and ADAR93-5 with the target sequence exhibited a positive effect on editing, shown by an increase of fluorescent signal when compared to oligonucleotides without the mismatch (ADAR93-2 and ADAR93-4, respectively). This indicates that an additional mismatch with position 4 upstream from the editing site (upstream=towards 5' in the target sequence) may assist ADAR proteins further to bind to target RNA which then leads to an increased efficiency in editing.

Example 3. RNA Editing in the Treatment of A1AT-Deficiency

Another disease target for RNA editing using the approach as outlined herein is A1AT-deficiency (A1ATD), caused by the c.1096G>A mutation in the SERPINA1 gene. The target is the human c.1096G>A mutant sequence for both in vitro and in vivo delivery. The mouse models contain a humanized sequence. For in vivo delivery, the main target of the constructs that are designed following the teaching of the present invention is the liver, as this is where most of the A1AT is produced. Evaluation is based on observed editing activity on the RNA level, as well as functional rescue of the lung and liver phenotypes associated with the disease.

Example 4. RNA Editing in the Treatment of Parkinson's Disease

A further disease target for RNA editing using the approach of the present invention is Parkinson's disease that is caused by the c.6055G>A mutation in the LRRK2 gene. This is the most common genetic cause linked to Parkinson's disease. Various methods are tested to target the brain with antisense oligonucleotides designed as presented herein, beginning with direct injections using a mouse model. Evaluation of efficacy is primarily based on the editing activity observed on the RNA level. The phosphoproteome of the cells are also studied, in order to establish that the hyperactive kinase activity (known to affect e.g. Rab GTPases) caused by the mutation is reversed. Ultimately, the effects on nigrostriatal dopaminergic neuron integrity of the mice is evaluated.

Example 5. RNA Editing by Endogenous ADAR

To investigate whether RNA editing could be achieved without overexpressing exogenous ADAR enzymes, it was first assessed what available cell lines express ADAR1 and/or ADAR2. These cells (if (over) expressing ADAR1 and/or ADAR2) would then be transfected with a construct comprising the GFP stop codon as outlined in Example 1, together with the oligonucleotides of interest, to edit the GFP stop. The following cell lines were initially tested for ADAR expression: A549 (human lung carcinoma), HCT116 (human colon carcinoma), T84 (human colon carcinoma), SNU-449 (human hepatocellular carcinoma), SNU-475 (human hepatocellular carcinoma), PANC1 (human pancreatic cancer), SK-N-SH (human neuroblastoma) and MCF7 (human breast carcinoma). A549 cells were kept in RPMl1640+ 10% FBS, HCT116 (ATCC#62765668) were kept in McCoy's 5A+10% FBS, T84 were kept in DMEM:F12 (1:1)+10% FBS, SNU-449 (ATCC#63014146) were kept in RPMl1640+10% FBS, SNU-475 (ATCC#62996846) were kept in RPMl1640+10% FBS, PANC1 were kept in DMEM+10% FBS, SK-N-SH were kept in MEME+10% FBS+5 ml/L NaPyr+5 ml/L Glutamax, and MCF7 cells were kept in DMEM+10% FBS. The expression of ADAR1 and ADAR2 in each cell line was checked using western blotting. For this, cells were harvested and protein quantification was performed using a Pierce BSA Protein Assay Kit (Thermo Scientific) using the manufacturer's protocol. Equal amounts of protein were separated on SDS-PAGE gel and transferred to membranes for analysis. Initially, blots were stained with Ponceau S to visualize total protein loading, which appeared to be equal for all cell lines/lanes (data not shown). Next, the membranes were washed 1× in PBS-T, incubated in 10 ml primary mouse anti-ADARB1 (SAB1405426 (Sigma); 1:1000 in 0.05% PBS-T) and mouse anti-ADAR1 (GT1066 ab 184527 (Abcam) 1:1000, in 0.05% PBS-T) and rabbit anti-tubulin (1:5000 in 0.05% PBS-T)) antibody solution on a roller bench O/N at 4° C. The next day the membranes were washed 3×5 min with PBS-T, and incubated for 1 h at RT with a 1:5000 anti-mouse IRDye 800CW and a 1:5000 anti-rabbit IRDye 680RD secondary antibody solution. The membranes were washed 3×5 min with PBS-T and then 5 min with PBS. The membranes were scanned using the Oddysey CLx imaging system (LiCor Bioscence) with the 700 and 800 wavelength and automatic imaging settings.

Figure 6:
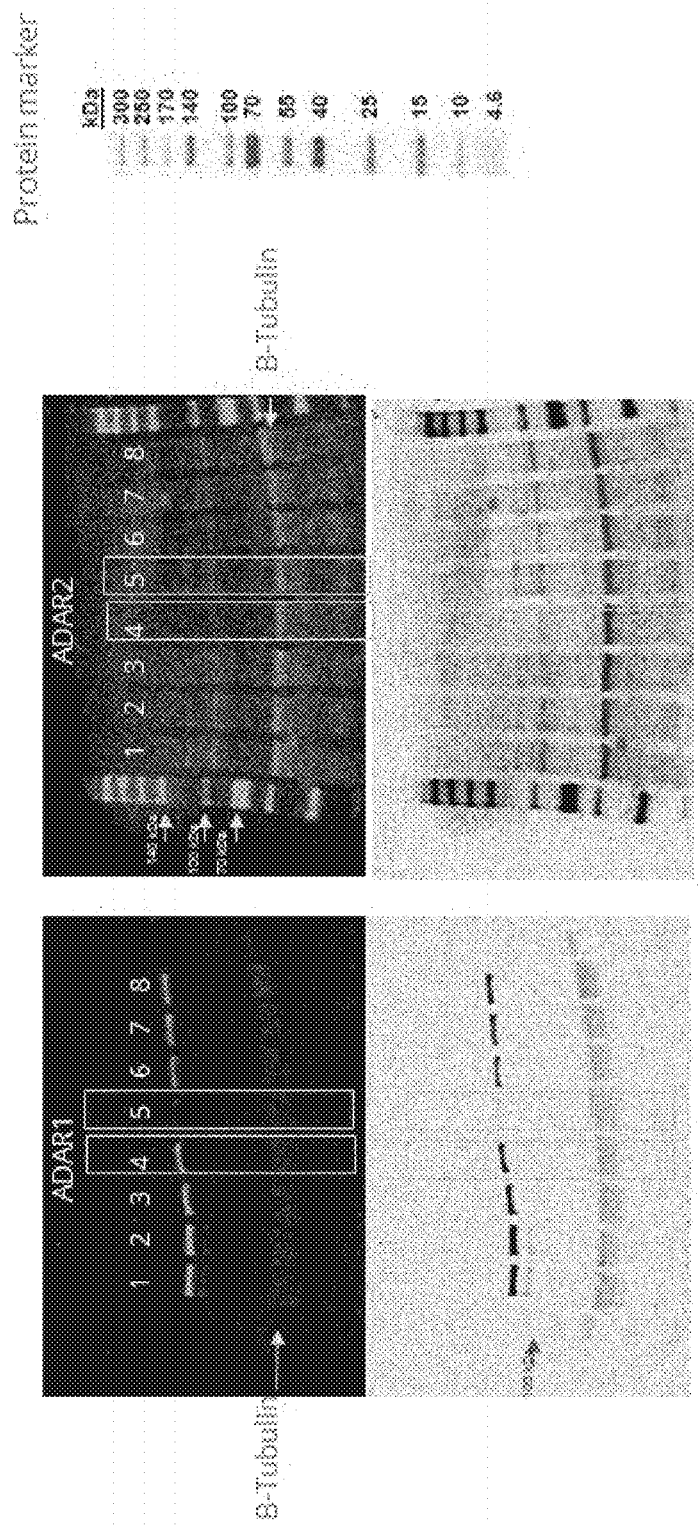
FIG. 6 is a western blot of eight different human cancer cell lines (lane numbering according to the table in the bottom panel), assessing the expression of ADAR1 and ADAR2, for subsequent analysis of endogenous ADAR activity.
Figure 10B:
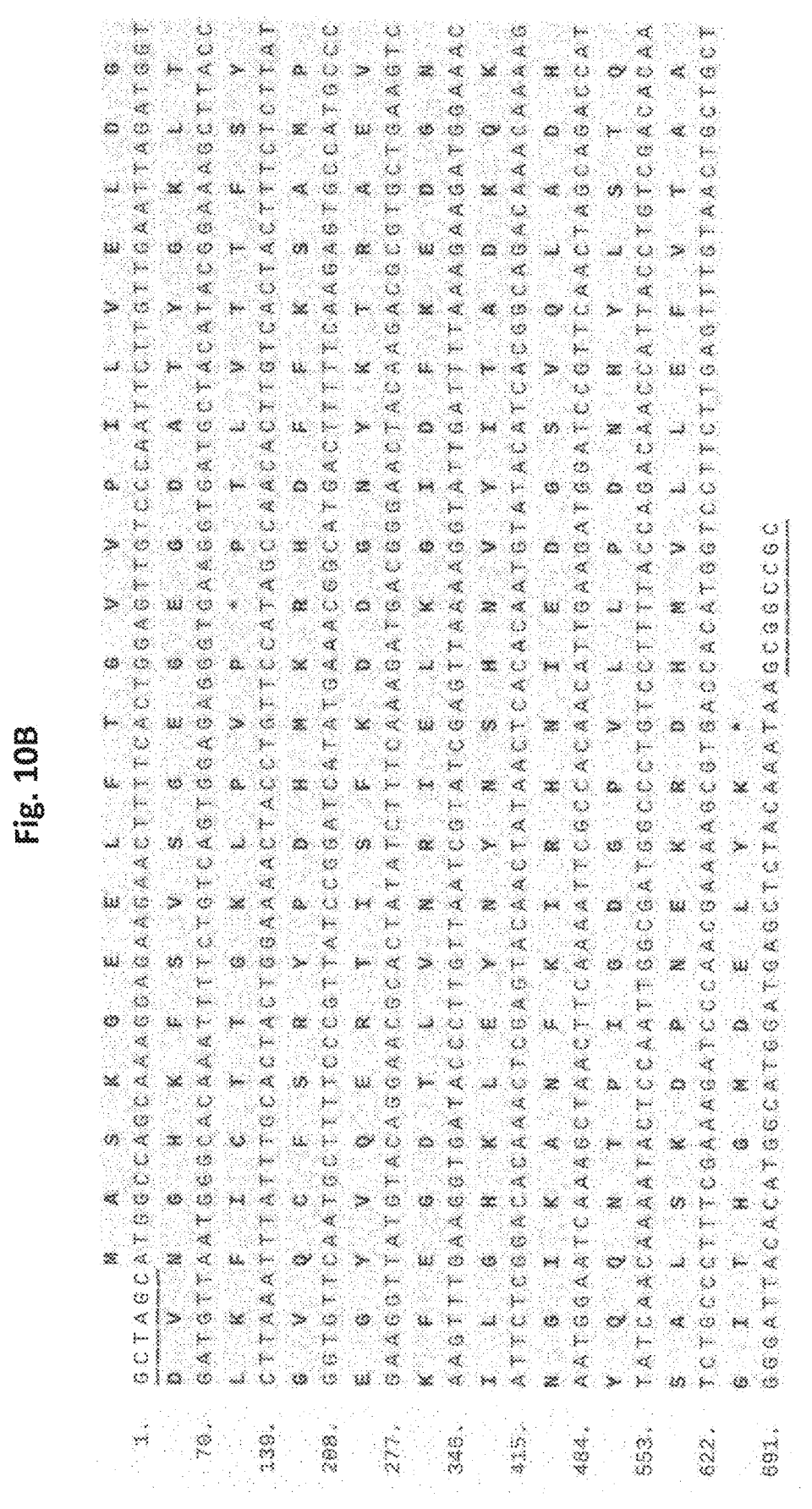

The western blots are shown in FIG. 6. Whereas the protein loading was equivalent for all cell lines as can be deduced from the B-Tubulin expression, it appears that ADAR1 expression is similar for all cell lines except for the human breast cancer cell line MCF7 in which the expression is significantly lower. On the other hand, the ADAR2 expression is similar for all cell lines except for the human hepatocellular carcinoma SNU-475, where it appears to be present but significantly less abundant. The other 6 cell lines appear to express ADAR1 and ADAR2 to comparable levels. Since all cell lines turned out to express ADAR1 or ADAR2 or both ADAR1 and ADAR2, all cells except T84 that appeared difficult to transfect, were tested to see whether these endogenous levels of the RNA editing enzymes were sufficient to edit RNA at a predetermined position in a target sequence. For this cells were transfected with a target sequence (GFPstop57) and oligonucleotides. The GFPstop57 expression construct (FIG. 10A) is the same construct as was used in the generation of the HeLa cell line (example 1) with the stably integrated GFPstop57 sequence (SEQ ID NO:9; FIG. 10B) that encodes a 57 amino acid protein due to a stop at residue 58 (SEQ ID NO:10 for the amino acid sequence; FIG. 10B).

Cells were plated with approximately $0.3 \times 10^6$ cells per well in a 6-well plate in 2 ml Medium. 24 hr after plating cells were transfected with 1000 ng GFPstop57 plasmid using Lipofectamine 2000 (Invitrogen) and Opti-Mem (Gibco) applying general technologies known to the person skilled in the art. 6 h after this transfection 2 ml fresh medium was added and 48 h after the plating, cells were transfected with 100 nM oligonucleotide, and again 6 h later 2 ml fresh medium was added. Cells were collected 30 h after the transfection with the oligonucleotide. A scrambled oligo, and Mock (Cy5) transfections were taken along as negative controls. The following antisense oligonucleotides were tested, similar to what is shown in Example 1 and FIG. 1 and SEQ ID NO's 1 to 4, respectively:

ADAR56-2

-continued

ADAR57-2
5'-g*a*a*a*guagugagaaguguuggCCAuggaacagguuguuuuc*c*a*g*u-3'

ADAR58-2
5'-g*a*a*a*gucucgacaaguguuggCCAuggaacagguacaauuc*c*a*g*u-3'

ADAR59-2
5'-c*a*u*u*gaagaagauaagagaaaguacugagaaguguuggCCAug gaacag*g*u*a*g-3'

The lower case are 2'-O methyl modified RNA nucleotides, the upper case nucleotides are unmodified RNA nucleotides (hence, no 2'-O methyl modification) and surround the center C that is opposite the target adenosine in GFPstop57. The asterisks (*) depict the phosphorothioate linkages between nucleosides at the termini of the oligonucleotides.

Figure 7:
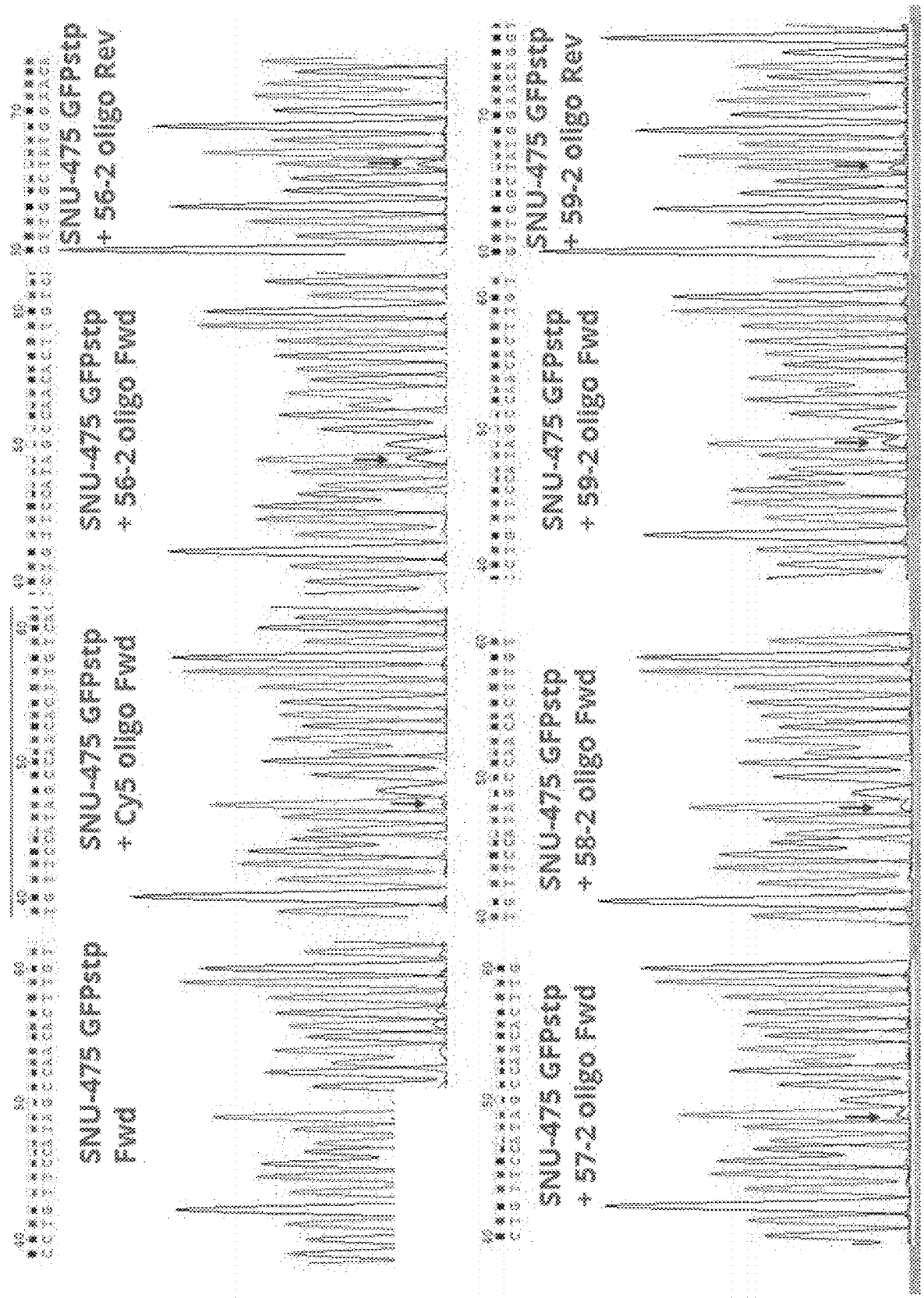
FIG. 7 shows the sequencing results of the PCR product derived from a GFPstop57 target plasmid that was incubated with four different antisense oligonucleotides (ADAR56-2, ADAR57-2, ADAR58-2 and ADAR59-2, abbreviated here to 56-2, 57-2, 58-2 and 59-2 respectively) in SNU-475 liver cancer cells. ADAR59-2=ADAR59. RNA editing has taken place without the need of over-expressing ADAR enzymes. 'Fwd'=forward sequencing; 'Rev'=reverse sequencing. The spot of the target adenosine (shifting to a guanosine in a forward sequence and a cytidine in a reverse sequence) is given by an arrow.
Figure 8:
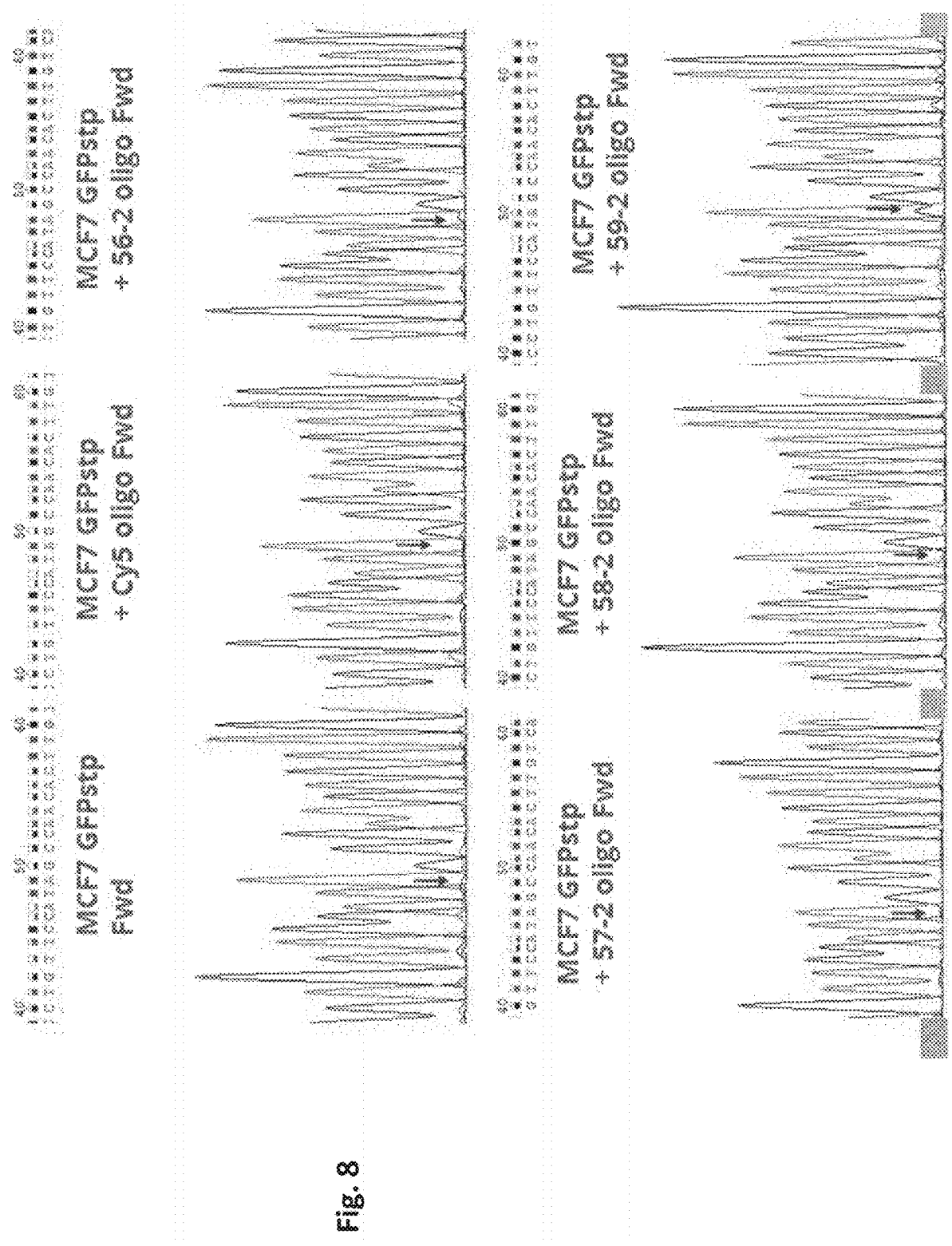
FIG. 8 shows the sequencing results of the PCR product derived from a GFPstop57 target plasmid that was incubated with four different antisense oligonucleotides (ADAR56-2, ADAR57-2, ADAR58-2 and ADAR59-2, abbreviated here to 56-2, 57-2, 58-2 and 59-2 respectively) in MCF7 breast cancer cells. RNA editing has taken place without the need of over-expressing ADAR enzymes. 'Fwd'=forward sequencing. The spot of the target adenosine (shifting to a guanosine) is given by an arrow. No significant shift was observed with ADAR56-2, ADAR57-2 and ADAR58-2, but a very significant RNA editing shift was observed with ADAR59-2.
Figure 9:
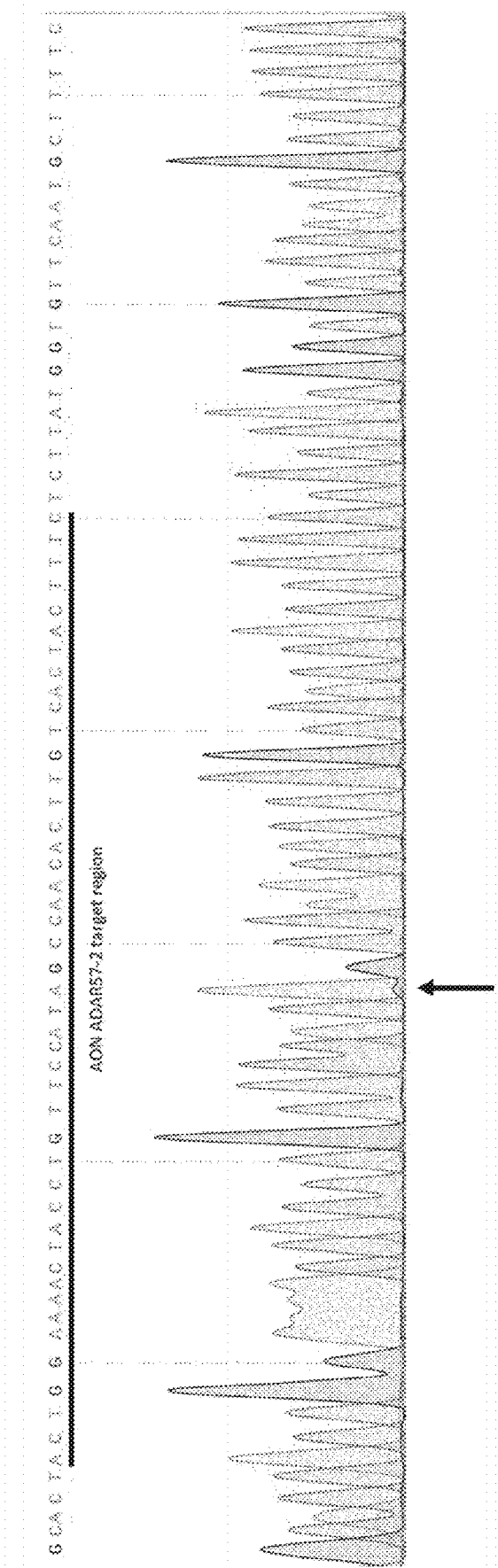
FIG. 9 shows the sequence data of the region surrounding the target adenosine (arrow) after treatment with ADAR57-2 (see also FIG. 7, bottom left), and shows that no deamination occurs at other adenosines in the vicinity of the target adenosine and in the target region of the AON.

36 h after transfection, RNA was isolated from lysed cells and used as a template for cDNA synthesis and PCR. RNA quality was checked with the Agilent 2100 bioanalyzer. Analysis of RNA editing was performed by RT-PCR as outlined in example 1, followed by Sanger sequencing of the PCR product, using general RT-PCR and sequencing methods known to the person skilled in the art. RT-PCR revealed that all 5 remaining cell lines that were transfected with the GFPstop57 construct and oligonucleotides (except for SK-N-SH cells that were transfected with ADAR59-2) did yield a 175 nucleotide product (data not shown). The PCR product from the different cell lines was used in sequence analysis using a GFP forward3 (SEQ ID NO:7, see above) and GFP reverse3 primer (SEQ ID NO:8, see above). In A549, HCT116 and PANC1 cells no significant shift from TAG->TGG (forward direction) or from CTA->CCA (reverse direction) could be detected above background levels, whereas in SNU-449 cells some shift was seen with ADAR56-2 and ADAR59-2 oligonucleotides (data not shown). The clearest results that were far above background were obtained with SNU-475 and MCF7 cells. FIG. 7 shows the results with the four oligonucleotides on SNU-475 (liver cancer) cells using the forward (FWD) and reverse (REV) primers in sequencing. FIG. 8 shows the results with the four oligonucleotides on MCF7 (breast cancer) cells using the forward (FWD) primer in sequencing. These figures display a very clear and significant shift in the sequence at the target position, wherein it appears that ADAR59-2 provided the best results in MCF7 while RNA editing with endogenous ADAR was observed in SNU-475 cells using all four oligonucleotides. FIG. 9 provides the sequencing results after use of ADAR57-2 (see also FIG. 7 left at the bottom) indicating that only at the target adenosine (arrow) deamination takes place, showing that no promiscuous editing occurs at surrounding adenosines and the AONs and methods of the present invention ensure very site-specific editing. These results show that the inventors of the present invention achieved RNA editing in cells in which a target sequence and an RNA-editing inducing oligonucleotide (with specific modifications) was introduced without the need to over-express an RNA editing enzyme, i.e. by relying on the enzymatic activity of endogenous ADAR proteins, and in a site-specific manner (i.e. only one adenosine within the RNA sequence targeted by the AON was edited; see FIG. 9).

Example 6. RNA Editing by Endogenous ADAR on an Endogenous Target

After achieving RNA editing using endogenous ADAR enzymes as outlined in Example 5, it was investigated whether RNA editing using endogenous ADAR enzymes could also be achieved without using the co-transfection of a target sequence. The inventors of the present invention selected Small Nuclear Ribonucleoprotein Polypeptide A (Snrpa) as an endogenous target due to its relatively high abundance and ubiquitous expression. The gene encodes for a protein that associates with stem loop II of the U1 small nuclear ribonucleoprotein, which binds the 5' splice site of precursor mRNAs and is required for splicing. AONs were designed to edit the wild type stop codon (UAG) of mouse Snrpa mRNA which would then likely lead to extension of the open reading frame and enlarged protein encoded by the downstream sequences (FIG. 11).

Two AONs were initially designed: ADAR87-1 and ADAR89-1 (see Table 2) and tested in Hepa 1-6 cells, which is a cell line derived of the BW7756 mouse hepatoma that arose in a C57/L mouse. Cells were plated in a 6-well plate 24 hours prior to the transfection of 200,000 cells/well in regular culture medium (DMEM+10% FCS). After 24 h cells were either not transfected (NT control and AON alone) or transfected with 1000 ng plasmid encoding the short isoform of ADAR2 (ADAR2sh) using Lipofectamine 2000 (Invitrogen) following the manufacturer's protocols. Medium was changed before adding the transfection mix and medium was refreshed in the wells without transfection. Again 24 h later cells were either not transfected again (NT control) or with a final concentration of 100 nM AON per well of ADAR87-1 or ADAR89-1. Medium was refreshed before transfection.

Cells were incubated for 48 h after the second transfection (or in the case of AON alone, after the single transfection) at 37° C. Medium was removed and cells were washed once with 1×PBS and 400 µl Trizol was added to each well for cell lysis. The Trizol was then collected in 1.5 mL Eppendorf tubes and RNA was extracted with the Direct-Zol RNA miniprep (Zymo) following the instructions provided by the manufacturer. RNA concentrations were measured using the Nanodrop and 500 ng RNA was used for cDNA synthesis with the Maxima Reverse Transcriptase kit (ThermoFisher Scientific). In a first step, the AONs were dissociated from the target mRNA by incubation with 1.2 µl (2 µM) partly complementary sense oligonucleotide mSnrpa-SON3: 5'-U*C*C*U*UUGCCAAGAAGUGGCACCUUUUCCUCCCAUGCCUACUCC*3' (SEQ ID NO:20). The asterisks in mSnrpa-SON3 indicate the internucleoside phosphorothioate linkages. All nucleotides in this oligonucleotide are 2'-O-methylated. cDNA synthesis was performed using the protocols of the manufacturer. PCR was performed using forward primer Fw1_mSNRPA 5'-GCCTTCGTGGAGTTTGACA-3' (SEQ ID NO:21) and reverse primer Rev1_mSNRPA 5'-ACACACGGCTCTGAGAAGGT-3' (SEQ ID NO:22) using methods generally known to the person skilled in the art. PCR product was checked on an Agilent 2100 Bioanalyser and purified with the Nucleo-Spin Gel and PCR clean-up kit (Macherey-Nagel) and purified products were sequenced with the sequencing primer Snrp-1-Fw1 5'-CGTG-GAGTTTGACAATGAAGT-3' (SEQ ID NO:23).

TABLE 2

A, C, G, and U are RNA; underlined C and A are DNA; mA, mC, mG, and mU are 2'-O methylated ribonucleotides; asterisks indicate phosphorothioate linkages.

| Name | Plain sequence (5' to 3') | Sequence w/ modifications (5' to 3') |
|---|---|---|
| ADAR87-1 (SEQ ID NO: 18) | GUAGGCAUGGGAGGAAAAG GUGCCACUUCUUGGCAAAG GA | mG*mU*mA*mG*mGmCmAmUmGmGmA mGmGmAmAmAmAmGmGmUmGCCAmCmU mUmCmUmUmGmGmCmA mA*mA*mG*mG*mA |
| ADAR89-1 (SEQ ID NO: 19) | GACUGAGGUACUCCAUAGG GAAAGGUGCCACUUCUUGG CAAAGGA | mG*mA*mC*mU*mGmAmGmGmUmAmCmU mCmCmAmUmAmGmGmGmAmAmAmGmGmU mGCCAmCmUmUmCmUmUmGmGmCmA mA*mA*mG*mG*mA |
| ADAR89-2 (SEQ ID NO: 32) | GACUGAGGUACUCCAUAGG GAAAGGUGCCACUUCUUGG CAAAGGA | mG*mA*mC*mU*mGmAmGmGmUmAmCmU mCmCmAmUmAmGmGmGmAmAmAmGmGmU mGCCAmCmUmUmCmUmUmGmGmCmA mA*mA*mG*mG*mA |
| ADAR94-1 (SEQ ID NO: 33) | GACUGAGGUACUCCUUAGA GAAAGGUGCCACUUCUUGG CAAAGGA | mG*mA*mC*mU*mGmAmGmGmUmAmCmU mCmCmUmUmAmGmAmGmAmAmAmGmGmU mGCCAmCmUmUmCmUmUmGmGmCmA mA*mA*mG*mG*mA |

Figure 12:
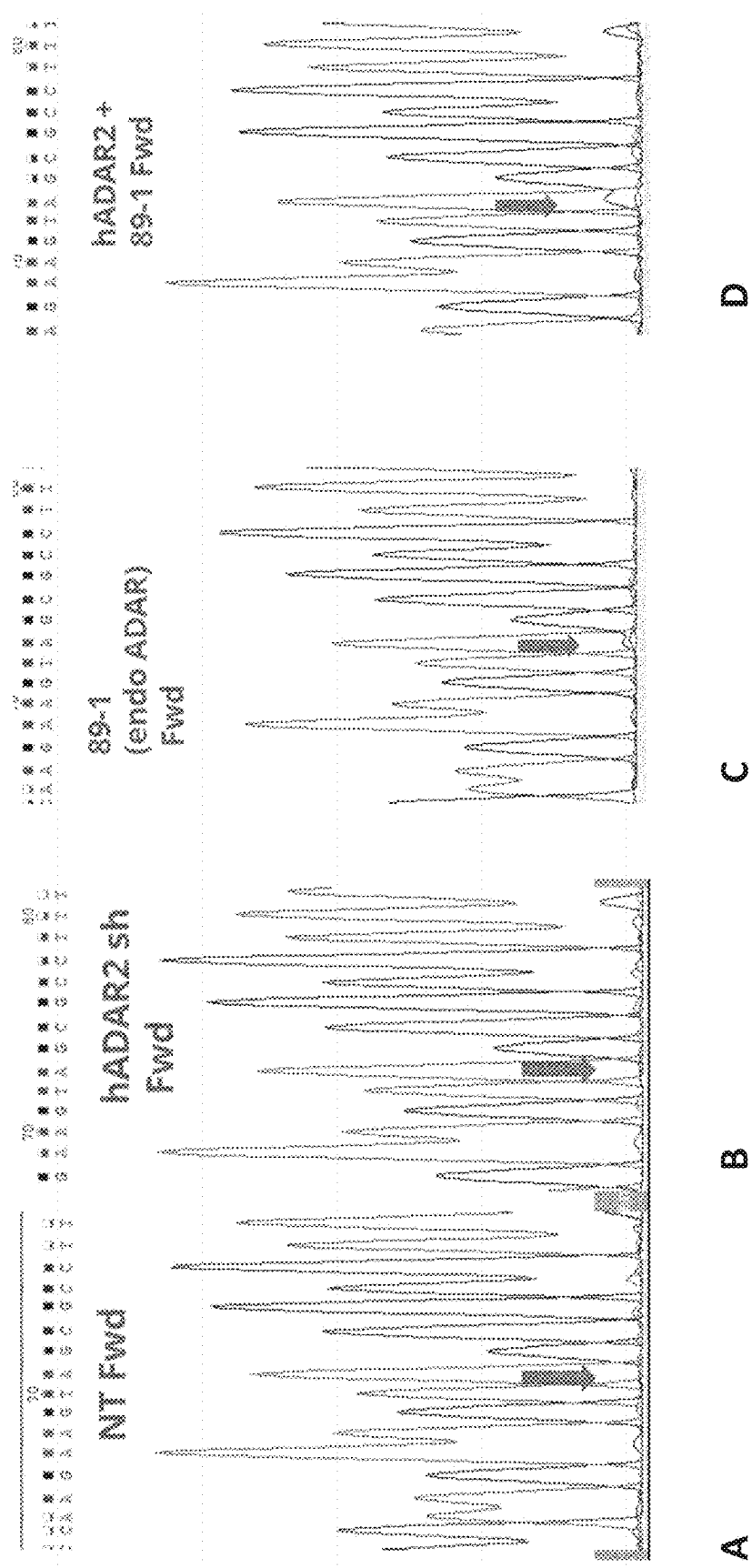
FIG. 12 shows the results of RNA editing on endogenous SNRPA RNA in mouse Hepa 1-6 cells using an AON. Panel (A) shows the non-transfected (NT) control. Panel (B) shows the control in which only the plasmid encoding the short isoform of ADAR2 was transfected. Panel (C) shows a rise in the G peak indicated by an arrow that indicates that (A to I) RNA editing has taken place at the desired position after transfection with ADAR89-1 AON, in cells that were not transfected with ADAR2 over-expressing plasmid. Panel (D) shows the positive control with both the ADARsh expression plasmid and the AON.

No editing above background was observed when ADAR87-1 was used (data not shown). The results of the RNA editing caused by ADAR89-1 oligonucleotide are provided in FIG. 12. Panel (A) shows the non-transfected (NT) control without any detectable RNA editing at the stop codon position (given by an arrow). Panel (B) shows the control in which only the plasmid encoding the short isoform of ADAR2 was transfected. Panel (C) shows a rise in the G peak indicated by an arrow. This increase that is clearly above background indicates that (A->I) RNA editing has taken place at the desired position after transfection with only ADAR89-1 AON, in cells that were not transfected with ADAR2 over-expressing plasmid. Panel (D) shows the positive control with both the ADARsh expression plasmid and the AON. It is believed that this result (panel C) is the first time that induced RNA editing has ever been observed specifically at a desired position by introduction of an antisense oligonucleotide in the absence of ADAR over-expression and without co-transfection of plasmids that cause the overexpression of target RNA.

Figure 13:
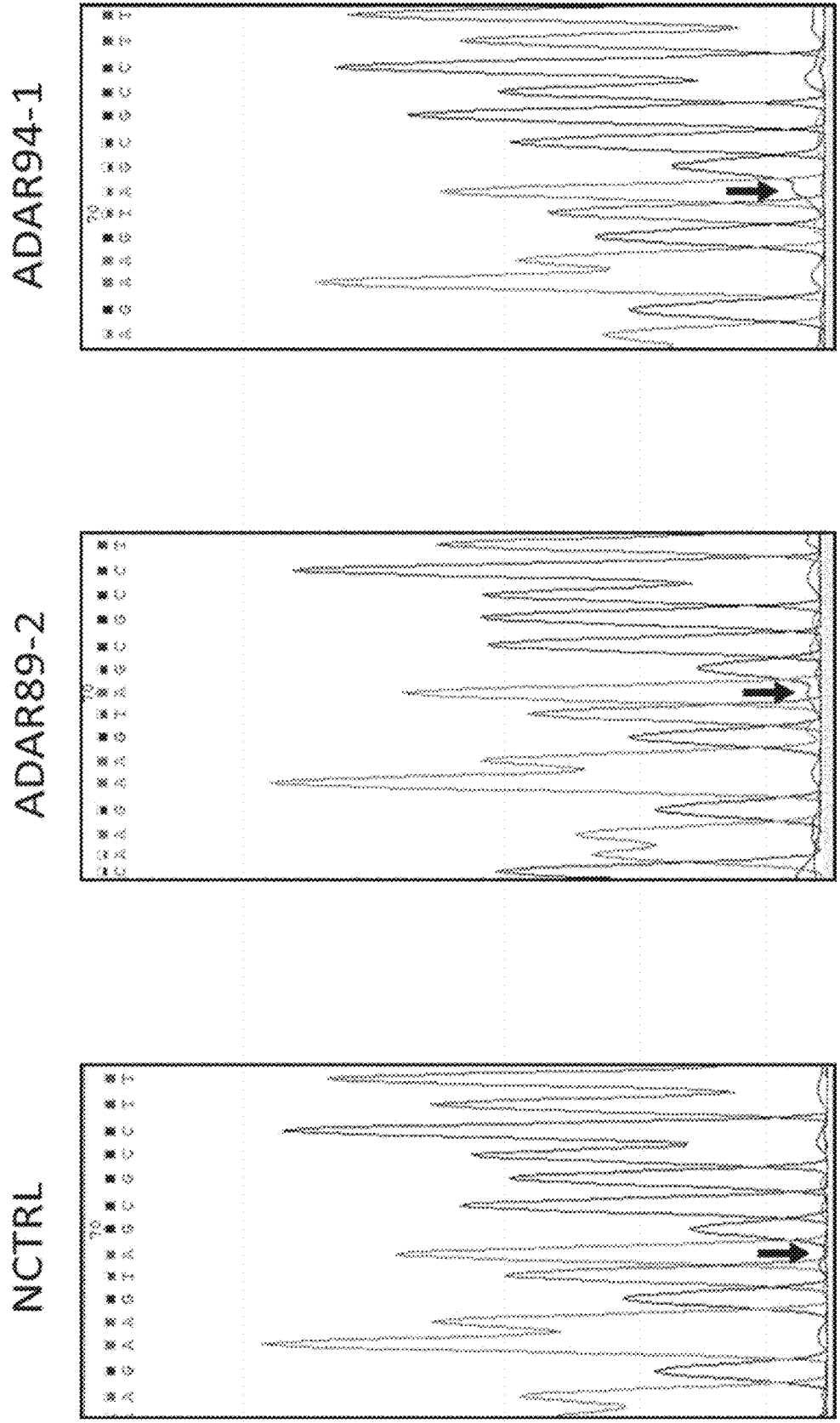
FIG. 13 shows the sequencing results after introduction of ADAR89-2 and ADAR94-1 AONs in mouse Hepa 1-6 cells and shows that RNA editing can be achieved with AONs that have DNA nucleosides in the Central Triplet opposite the targeted adenosine, and that such RNA editing may be further increased when additional mismatches are introduced.

Two further oligonucleotides were designed: ADAR89-2 and ADAR94-1 (see Table 2) wherein the Central Triplet CCA (the middle nucleotide C is opposite to the to-be-edited adenosine) is DNA while the rest of the oligonucleotide is 2'-O-methyl-modified. The sequence of ADAR89-2 is identical to ADAR89-1, whereas the sequence of ADAR94-1 has two additional mismatches in comparison to ADAR89-2 (see FIG. 12). These AONs were tested in the same assay as described in this example above in Hepa 1-6 cells. The resulting sequencing data is depicted in FIG. 13 and shows that no RNA editing is detected for the non-transfected control (NCTRL). The sequencing data for oligonucleotide ADAR89-2 shows presence of a G nucleotide at the editing site as indicated by arrow, which shows that also when the Central Triplet is DNA (not RNA) good editing can be obtained. Replacing the central triplet RNA nucleotides, which are very sensitive to nucleases, with DNA can add to the stability of the AON. A clear increase of the signal for G peak for oligonucleotide ADAR94-1 indicates that insertion of two additional mismatches in the positions 10 and 14 in the sequence of ADAR89-2 has an even more positive effect on editing of the endogenous Snrpa pre-mRNA, which again shows that additional bulges, mismatches and/or wobbles can further increase RNA editing efficiency (which in all different targets very likely depends on a multiplicity of factors, such as sequence, melting temperature of the AON-RNA helix, overlap, secondary structures, etc.).

Example 7. RNA Editing to Repair the Val66Met Mutation in RNA Encoding BDNF

The design of single-stranded RNA editing inducing oligonucleotides can be used for a variety of RNA targets and a variety of diseases and disorders related to such targets comprising the mutation. One of the recently identified potential targets for Alzheimer's disease is the Brain-Derived Neurotrophic Factor (BDNF) Val66Met polymorphism that is also caused by a G to A mutation (Boots et al. Neurology May 30, 2017. Vol 88(22):2098-2106). AONs as disclosed herein, are used to edit the RNA at the specific BDNF mRNA position. AONs that are used for such purpose have the following sequences (with the lowers strand being the BDNF target sequence (SEQ ID NO:35) and the upper strands representing the oligonucleotides. Modifications are 2'-O-methyl (lower case), DNA (upper case), phosphorothioate linkages (asterisks) and mismatches and wobbles (underlined). The target adenosine is given in bold.

BDNF AON1
(SEQ ID NO: 36)
3'-CUGUGAAAGCUUGUGCAUUAUCUUCUCGACAACCUACUCCUGGUCUU
UCAAG-5

5'-AUCAUUGGCUGACACUUUCGAACACAUGAUAGAAGAGCUGUUGGAUG
AGGACCAGAAAGUUCGGCCCAAUG-3'

5'-g*a*a*c*uuucugguccucauccaacagcucuucuauuACGuguuc
gaaag*u*g*u*c-3'

BDNF AON2
(SEQ ID NO: 37)
3'-CUGUGAAAGCUUGUICAUUAUCUUCUCGACAACCUACUCCUGGUCUU
UCAAG-5

-continued

```
5'-AUCAUUGGCUGACACUUUCGAACACAUGAUAGAAGAGCUGUUGGAUG

AGGACCAGAAAGUUCGGCCCAAUG-3'

5'-g*a*a*c*uuucugguccucauccaacagcucuucuauuACIuguuc gaaag*u*g*u*c-3'

BDNF AON3
                                          (SEQ ID NO: 38)
3'-CUGUGAAAGCUUGUGCAUUAUCUUCUCGUCAAACUACUCCUGUAAUU
```

-continued

```
UCAAG-5

5'-AUCAUUGGCUGACACUUUCGAACACAUGAUAGAAGAGCUGUUGGAUG

AGGACCAGAAAGUUCGGCCCAAUG-3'

5'-g*a*a*c*uuuaauguccucaucaaacugcucuucuauuACGuguuc gaaag*u*g*u*c-3'
```

It will be understood that the invention is described above by way of example only and modifications may be made whilst remaining within the scope and spirit of the invention.

---

The invention claimed is:

1. An antisense oligonucleotide (AON) capable of forming a double stranded complex with a target RNA in a cell for the deamination of a target adenosine present in the target RNA by an ADAR enzyme present in the cell, wherein:
   (a) the AON is complementary to a target RNA region comprising the target adenosine, and the AON comprises one or more mismatches, wobbles and/or bulges with the complementary target RNA region;
   (b) the AON comprises one or more nucleotides with one or more sugar modifications, provided that the nucleotide opposite the target adenosine comprises a ribose with a 2'-OH group, or a deoxyribose with a 2'-H group;
   (c) the AON does not comprise a portion that is capable of forming an intramolecular stem-loop structure capable of binding an ADAR enzyme;
   (d) the AON does not include a 5'-terminal O6-benzylguanine modification;
   (e) the AON does not include a 5'-terminal amino modification; and
   (f) the AON is not covalently linked to a SNAP-tag domain.

2. An AON capable of forming a double stranded complex with a target RNA in a cell for the deamination of a target adenosine present in the target RNA by an ADAR enzyme present in the cell, wherein:
   (a) the AON is complementary to a target RNA region comprising the target adenosine, and the AON comprises one or more mismatches, wobbles and/or bulges with the complementary target RNA region;
   (b) the AON comprises one or more nucleotides with one or more sugar modifications, provided that the nucleotide opposite the target adenosine comprises a ribose with a 2'-OH group, or a deoxyribose with a 2'-H group;
   (c) the AON does not comprise a portion that is capable of forming an intramolecular stem-loop structure capable of binding an ADAR enzyme; and
   (d) the AON is not a 17-mer or a 20-mer.

3. An AON capable of forming a double stranded complex with a target RNA in a cell for the deamination of a target adenosine present in the target RNA by an ADAR enzyme present in the cell, wherein:
   (a) the AON is complementary to a target RNA region comprising the target adenosine, and the AON comprises one or more mismatches, wobbles and/or bulges with the complementary target RNA region;
   (b) the AON comprises one or more nucleotides with one or more sugar modifications, provided that the nucleotide opposite the target adenosine comprises a ribose with a 2'-OH group, or a deoxyribose with a 2'-H group;
   (c) the AON does not comprise a portion that is capable of forming an intramolecular stem-loop structure capable of binding an ADAR enzyme; and
   (d) the AON is longer than 17 nucleotides, or shorter than 14 nucleotides.

4. An AON capable of forming a double stranded complex with a target RNA in a cell for the deamination of a target adenosine present in the target RNA by an ADAR enzyme present in the cell, wherein:
   (a) the AON is complementary to a target RNA region comprising the target adenosine;
   (b) the AON comprises one or more nucleotides with one or more sugar modifications, provided that the nucleotide opposite the target adenosine comprises a ribose with a 2'-OH group, or a deoxyribose with a 2'-H group;
   (c) the AON does not comprise a portion that is capable of forming an intramolecular stem-loop structure that is capable of binding an ADAR enzyme;
   (d) the AON comprises 1, 2, 3, 4, 5, 6, 7, 8, 9 or 10 mismatches, wobbles and/or bulges with the complementary target RNA region.

5. The AON of claim 1, wherein the nucleotide opposite the target adenosine is a cytidine, a deoxycytidine, a uridine, or a deoxyuridine.

6. The AON of claim 1, wherein the nucleotide directly 5' and/or 3' from the nucleotide opposite the target adenosine comprises a ribose with a 2'-OH group, or a deoxyribose with a 2'-H group.

7. The AON of claim 6, wherein all other nucleotides in the AON comprise a 2'-O-alkyl group.

8. The AON of claim 1, comprising at least one phosphorothioate linkage.

9. The AON of claim 8, wherein the 2, 3, 4, 5, or 6 terminal nucleotides of the 5' and 3' terminus of the AON are linked with a phosphorothioate linkage.

10. The AON of claim 9, wherein the 5 terminal nucleotides of the 5' and 3' terminus of the AON are linked with phosphorothioate linkages.

11. The AON of claim 1, wherein the AON is longer than 10, 11, 12, 13, 14, 15, 16 or 17 nucleotides.

12. The AON of claim 1, wherein the AON is shorter than 100 nucleotides.

13. The AON of claim 1, wherein the AON comprises 18 to 70 nucleotides.

14. A pharmaceutical composition comprising the AON of claim 1 and a pharmaceutically acceptable carrier.

15. A method of treating or preventing a genetic disorder in a subject in need thereof, the method comprising administering the AON of claim 1 to the subject.

16. A method of deaminating at least one target adenosine present in a target RNA in a cell, the method comprising:
   (i) contacting a cell with the AON of claim 1 thereby to permit the AON to enter the cell and an ADAR enzyme comprising a natural dsRNA binding domain to deaminate the target adenosine in the target RNA to an inosine; and
   (ii) optionally identifying the presence of the inosine in the targeted RNA.

17. The method of claim 16, wherein step (ii) comprises:
   (a) sequencing the targeted RNA sequence;
   (b) assessing the presence of a functional, elongated, full length and/or wild type protein when the target adenosine is located in a UGA or UAG stop codon, which is edited to a UGG codon through the deamination;
   (c) assessing the presence of a functional, elongated, full length and/or wild type protein when two target adenosines are located in a UAA stop codon, which is edited to a UGG codon through the deamination of both target adenosines;

(d) assessing whether splicing of the pre-mRNA was altered by the deamination; or (e) using a functional read-out, wherein the target RNA after the deamination encodes a functional, full length, elongated and/or wild type protein.

18. The AON of claim 1, wherein the target RNA sequence encodes CFTR, CEP290, alpha1-antitrypsin (A1AT), LRRK2, BDNF, or wherein the target RNA is encoded by the IDUA gene.

19. The AON of claim 7, wherein all other nucleotides in the AON comprise a 2'-O-methyl group.

20. The method of claim 15, wherein the genetic disorder is selected from the group consisting of: Cystic fibrosis, Hurler Syndrome, alpha-1-antitrypsin (A1AT) deficiency, Parkinson's disease, Alzheimer's disease, albinism, Amyotrophic lateral sclerosis, Asthma, ß-thalassemia, Cadasil syndrome, Charcot-Marie-Tooth disease, Chronic Obstructive Pulmonary Disease (COPD), Distal Spinal Muscular Atrophy (DSMA), Duchenne/Becker muscular dystrophy, Dystrophic Epidermolysis bullosa, Epidermylosis bullosa, Fabry disease, Factor V Leiden associated disorders, Familial Adenomatous, Polyposis, Galactosemia, Gaucher's Disease, Glucose-6-phosphate dehydrogenase, Haemophilia, Hereditary Hematochromatosis, Hunter Syndrome, Huntington's disease, Inflammatory Bowel Disease (IBD), Inherited polyagglutination syndrome, Leber congenital amaurosis, Lesch-Nyhan syndrome, Lynch syndrome, Marfan syndrome, Mucopolysaccharidosis, Muscular Dystrophy, Myotonic dystrophy types I and II, neurofibromatosis, Niemann-Pick disease type A, B and C, NY-esol related cancer, Peutz-Jeghers Syndrome, Phenylketonuria, Pompe's disease, Primary Ciliary Disease, Prothrombin mutation related disorders, such as the Prothrombin G20210A mutation, Pulmonary Hypertension, Retinitis Pigmentosa, Sandhoff Disease, Severe Combined Immune Deficiency Syndrome (SCID), Sickle Cell Anemia, Spinal Muscular Atrophy, Stargardt's Disease, Tay-Sachs Disease, Usher syndrome, X-linked immunodeficiency, and cancer.

* * * * *